US008754034B2

(12) United States Patent
Eisenberg et al.

(10) Patent No.: US 8,754,034 B2
(45) Date of Patent: Jun. 17, 2014

(54) STRUCTURE-BASED DESIGN OF PEPTIDE INHIBITORS OF AMYLOID FIBRILLATION

(75) Inventors: David S. Eisenberg, Los Angeles, CA (US); Stuart A. Sievers, Van Nuys, CA (US); John Karanicolas, St. Lawrence, KS (US); David Baker, Seattle, WA (US)

(73) Assignees: The Regents of the University of California, Oakland, AL (US); University of Washington, Seattle, WA (US)

( * ) Notice: Subject to any disclaimer, the term of this patent is extended or adjusted under 35 U.S.C. 154(b) by 583 days.

(21) Appl. No.: 12/702,175

(22) Filed: Feb. 8, 2010

(65) Prior Publication Data

US 2010/0204085 A1    Aug. 12, 2010

Related U.S. Application Data

(60) Provisional application No. 61/150,475, filed on Feb. 6, 2009.

(51) Int. Cl.
*A61K 38/02* (2006.01)
*C07K 2/00* (2006.01)
*A61P 25/28* (2006.01)

(52) U.S. Cl.
USPC ........ 514/1.1; 514/17.8; 514/18.1; 514/19.2; 530/300

(58) Field of Classification Search
None
See application file for complete search history.

(56) References Cited

U.S. PATENT DOCUMENTS

2005/0271650 A1*  12/2005  Freimark et al. ........... 424/130.1

OTHER PUBLICATIONS

Thompson et al,The 3D profile method for identifying fibril-forming segments of proteins, PNAS, 2006, 103, pp. 4074-4078.*
Nanga et al, NMR Structure in a Membrane Environment Reveals Putative Amyloidogenic Regions of the SEVI Precursor Peptide PAP248-286, J. Am. Chem. Soc., 2009, 131, pp. 17972-17979.*
Avila, J. (2000). Tau aggregation into fibrillar polymers: taupathies. FEBS Lett 476, 89-92.
Barghorn, S., Biernat, J., and Mandelkow, E. (2005). Purification of recombinant tau protein and preparation of Alzheimer-paired helical filaments in vitro. Methods Mol Biol 299, 35-51.
Berriman, J., Serpell, L. C., Oberg, K. A., Fink, A. L., Goedert, M., and Crowther, R. A. (2003). Tau filaments from human brain and from in vitro assembly of recombinant protein show cross-beta structure. Proc Natl Acad Sci U S A 100, 9034-9038.
Biernat, J. et al. (1992). The switch of tau protein to an Alzheimer-like state includes the phosphorylation of two serine-proline motifs upstream of the microtubule binding region. Embo J 11, 1593-1597.

Chalifour, R. J., McLaughlin, R. W., Lavoie, L., Morissette, C., Tremblay, N., Boule, M., Sarazin, P., Stea, D., Lacombe, D., Tremblay, P., and Gervais, F. (2003). Stereoselective interactions of peptide inhibitors with the beta-amyloid peptide. J Biol Chem 278, 34874-34881.
Cruz, M., Tusell, J. M., Grillo-Bosch, D., Albericio, F., Serratosa, J., Rabanal, F., and Giralt, E. (2004). Inhibition of beta-amyloid toxicity by short peptides containing N-methyl amino acids. J Pept Res 63, 324-328.
Dobson, C. M. (1999). Protein misfolding, evolution and disease. Trends Biochem Sci 24, 329-332.
Doig, A. J., Hughes, E., Burke, R. M., Su, T. J., Heenan, R. K., and Lu, J. (2002). Inhibition of toxicity and protofibril formation in the amyloid-beta peptide beta(25-35) using N-methylated derivatives. Biochem Soc Trans 30, 537-542.
Eanes, E. D., and Glenner, G. G. (1968). X-ray diffraction studies on amyloid filaments. J Histochem Cytochem 16, 673-677.
Esteras-Chopo, A., Pastor, M. T., Serrano, L., and Lopez de la Paz, M. (2008). New Strategy for the Generation of Specific d-Peptide Amyloid Inhibitors. J Mol Biol. 377, 1372-1381.
Ferrao-Gonzales, A. D., Robbs, B. K., Moreau, V. H., Ferreira, A., Juliano, L., Valente, A. P., F. C., Silva, J. L., and Foguel, D. (2005). Controlling {beta}-amyloid oligomerization by the use of naphthalene sulfonates: trapping low molecular weight oligomeric species. J Biol Chem 280, 34747-34754.
Findeis, M. A., Musso, G. M., Arico-Muendel, C. C., Benjamin, H. W., Hundal, A. M., Lee, J. J., Chin, J., Kelley, M., Wakefield, J., Hayward, N. J., and Molineaux, S. M. (1999). Modified-peptide inhibitors of amyloid beta-peptide polymerization. Biochemistry 38, 6791-6800.
Friedhoff, P., Schneider, A., Mandelkow, E. M., and Mandelkow, E. (1998). Rapid assembly of Alzheimer-like paired helical filaments from microtubule-associated protein tau monitored by fluorescence in solution. Biochemistry 37, 10223-10230.
Goedert, M., Spillantini, M. G., and Davies, S. W. (1998). Filamentous nerve cell inclusions in neurodegenerative diseases. Curr Opin Neurobiol 8, 619-632.

(Continued)

*Primary Examiner* — Julie Ha
*Assistant Examiner* — Li Ni Komatsu
(74) *Attorney, Agent, or Firm* — Venable LLP; Nancy J. Axelrod; Michael A. Gollin

(57) ABSTRACT

The invention provides methods for designing peptides that inhibit aggregation in target polypeptides. The candidate inhibitory peptidic compounds have an oligomeric sequence that forms energetically-favorable interactions with the amino acid sequence of the steric zipper region of the target protein, and also possess a zipper-disrupting feature that disrupt the peptide stacking at the steric zipper region. This method can be used to obtain inhibitory peptides to disrupt fibril formation involving any protein for which a steric zipper sequence can be identified. The invention also provides inhibitory peptidic compounds, which can be used in pharmaceutical compositions and methods for treating polypeptide aggregation-associated diseases or conditions.

14 Claims, 16 Drawing Sheets

(56) References Cited

OTHER PUBLICATIONS

Gordon, D. J., Sciarretta, K. L., and Meredith, S. C. (2001). Inhibition of beta-amyloid(40) fibrillogenesis and disassembly of beta-amyloid(40) fibrils by short beta-amyloid congeners containing N-methyl amino acids at alternate residues. Biochemistry 40, 8237-8245.
Goux, W. J., Kopplin, L., Nguyen, A. D., Leak, K., Rutkofsky, M., Shanmuganandam, V. D., Sharma, D., Inouye, H., and Kirschner, D. A. (2004). The formation of straight and twisted filaments from short tau peptides. J Biol Chem 279, 26868-26875.
Harkany, T., Mulder, J., Sasvari, M., Abraham, I., Konya, C., Zarandi, M., Penke, B., Luiten, P. G., and Nyakas, C. (1999). N-Methyl-D-aspartate receptor antagonist MK-801 and radical scavengers protect cholinergic nucleus basalis neurons against beta-amyloid neurotoxicity. Neurobiol Dis 6, 109-121.
Hughes, E., Burke, R. M., and Doig, A. J. (2000). Inhibition of toxicity in the beta-amyloid peptide fragment beta -(25-35) using N-methylated derivatives: a general strategy to prevent amyloid formation. J Biol Chem 275, 25109-25115.
Kapurniotu, A., Schmauder, A., and Tenidis, K. (2002). Structure-based design and study of non-amyloidogenic, double N-methylated IAPP amyloid core sequences as inhibitors of IAPP amyloid formation and cytotoxicity. J Mol Biol 315, 339-350.
Klabunde, T., Petrassi, H. M., Oza, V. B., Raman, P., Kelly, J. W., and Sacchettini, J. C. (2000). Rational design of potent human transthyretin amyloid disease inhibitors. Nat Struct Biol 7, 312-321.
Kokkoni, N., Stott, K., Amijee, H., Mason, J. M., and Doig, A. J. (2006). N-Methylated Peptide Inhibitors of beta Amyloid Aggregation and Toxicity. Optimization of the Inhibitor Structure. Biochemistry 45, 9906-9918.
Kondo, J., Honda, T., Mori, H., Hamada, Y., Miura, R., Ogawara, M., and Ihara, Y. (1988). The carboxyl third of tau is tightly bound to paired helical filaments. Neuron 1, 827-834.
Kortemme, T., Joachimiak, L. A., Bullock, A. N., Schuler, A. D., Stoddard, B. L., and Baker, D. (2004). Computational redesign of protein-protein interaction specificity. Nat Struct Mol Biol 11, 371-379.
Kuhlman, B., Dantas, G., Ireton, G. C., Varani, G., Stoddard, B. L., and Baker, D. (2003). Design of a novel globular protein fold with atomic-level accuracy. Science 302, 1364-1368.
LeVine, H., 3rd (1993). Thioflavine T interaction with synthetic Alzheimer's disease beta-amyloid peptides: detection of amyloid aggregation in solution. Protein Sci 2, 404-410.
Nelson, R., Sawaya, M. R., Balbirnie, M., Madsen, A. O., Riekel, C., Grothe, R., and Eisenberg, D. (2005). Structure of the cross-beta spine of amyloid-like fibrils. Nature 435, 773-778.
Ono, K., Hasegawa, K., Naiki, H., and Yamada, M. (2004). Curcumin has potent anti-amyloidogenic effects for Alzheimer's beta-amyloid fibrils in vitro. J Neurosci Res 75, 742-750.
Ono, K., Hasegawa, K., Naiki, H., and Yamada, M. (2004). Anti-amyloidogenic activity of tannic acid and its activity to destabilize Alzheimer's beta-amyloid fibrils in vitro. Biochim Biophys Acta 1690, 193-202.
Ono, K., Hasegawa, K., Yamada, M., and Naiki, H. (2002). Nicotine breaks down preformed Alzheimer's beta-amyloid fibrils in vitro. Biol Psychiatry 52, 880-886.
Ono, K., Yoshiike, Y., Takashima, A., Hasegawa, K., Naiki, H., and Yamada, M. (2004). Vitamin A exhibits potent antiamyloidogenic and fibril-destabilizing effects in vitro. Exp Neurol 189, 380-392.
Perez, M., Valpuesta, J. M., Medina, M., Montejo de Garcini, E., and Avila, J. (1996). Polymerization of tau into filaments in the presence of heparin: the minimal sequence required for tau-tau interaction. J Neurochem 67, 1183-1190.
Petrassi, H. M., Johnson, S. M., Purkey, H. E., Chiang, K. P., Walkup, T., Jiang, X., Powers, E. T., and Kelly, J. W. (2005). Potent and selective structure-based dibenzofuran inhibitors of transthyretin amyloidogenesis: kinetic stabilization of the native state. J Am Chem Soc 127, 6662-6671.
Petrassi, H. M. et al. (2000). Structure-Based Design of N-Phenyl Phenoxazine Transthyretin Amyloid Fibril Inhibitors. J Am Chem Soc 122, 2178-2192.
Rzepecki, P. et al. (2004). Prevention of Alzheimer's disease-associated Abeta aggregation by rationally designed nonpeptidic beta-sheet ligands. J Biol Chem 279, 47497-47505.
Sato, T. et al. (2006). Inhibitors of amyloid toxicity based on beta-sheet packing of Abeta40 and Abeta42. Biochemistry 45, 5503-5516.
Sawaya, M. R. et al. (2007). Atomic structures of amyloid cross-beta spines reveal varied steric zippers. Nature 447, 453-457.
Schumacher, T. N. et al. (1996). Identification of D-peptide ligands through mirror-image phage display. Science 271, 1854-1857.
Schweers, O. et al. (1995). Oxidation of cysteine-322 in the repeat domain of microtubule-associated protein tau controls the in vitro assembly of paired helical filaments. Proc Natl Acad Sci U S A 92, 8463-8467.
Selkoe, D. J. (2001). Alzheimer's disease: genes, proteins, and therapy. Physiol Rev 81, 741-766.
Sipe, J. D. and Cohen, A. S. (2000). Review: history of the amyloid fibril. J Struct Biol 130, 88-98.
Soto, C. et al. (1996). Inhibition of Alzheimer's amyloidosis by peptides that prevent beta-sheet conformation. Biochem Biophys Res Commun 226, 672-680.
Soto, C. et al. (1998). Beta-sheet breaker peptides inhibit fibrillogenesis in a rat brain model of amyloidosis: implications for Alzheimer's therapy. Nat Med 4, 822-826.
Studier, F. W. et al. (1990). Use of T7 RNA polymerase to direct expression of cloned genes. Methods Enzymol 185, 60-89.
Tatarek-Nossol, M., Yan, L. M., Schmauder, A., Tenidis, K., Westermark, G., and Kapurniotu, A. (2005). Inhibition of hIAPP amyloid-fibril formation and apoptotic cell death by a designed hIAPP amyloid- core-containing hexapeptide. Chem Biol 12, 797-809.
Tjernberg, L. O., Lilliehook, C., Callaway, D. J., Naslund, J., Hahne, S., Thyberg, J., Terenius, L., and Nordstedt, C. (1997). Controlling amyloid beta-peptide fibril formation with protease-stable ligands. J Biol Chem 272, 12601-12605.
Tjernberg, L. O., Naslund, J., Lindqvist, F., Johansson, J., Karlstrom, A. R., Thyberg, J., Terenius, L., and Nordstedt, C. (1996). Arrest of beta-amyloid fibril formation by a pentapeptide ligand. J Biol Chem 271, 8545-8548.
von Bergen, M., Friedhoff, P., Biernat, J., Heberle, J., Mandelkow, E. M., and Mandelkow, E. (2000). Assembly of tau protein into Alzheimer paired helical filaments depends on a local sequence motif ((306)VQIVYK(311)) forming beta structure. Proc Natl Acad Sci U S A 97, 5129-5134.
Westermark, P., Benson, M. D., Buxbaum, J. N., Cohen, A. S., Frangione, B., Ikeda, S., Masters, C. L., Merlini, G., Saraiva, M. J., and Sipe, J. D. (2007). A primer of amyloid nomenclature. Amyloid 14, 179-183.
Wiesehan, K., Buder, K., Linke, R. P., Patt, S., Stoldt, M., Unger, E., Schmitt, B., Bucci, E., and Willbold, D. (2003). Selection of D-amino-acid peptides that bind to Alzheimer's disease amyloid peptide abeta1-42 by mirror image phage display. Chembiochem 4, 748-753.
Wiesehan, K. et al. (2008). Inhibition of cytotoxicity and amyloid fibril formation by a D-amino acid peptide that specifically binds to Alzheimer's disease amyloid peptide. Protein Eng Des Sel. 21, 241-246.
Wille, H., Drewes, G., Biernat, J., Mandelkow, E. M., and Mandelkow, E. (1992). Alzheimer-like paired helical filaments and antiparallel dimers formed from microtubuleassociated protein tau in vitro. J Cell Biol 118, 573-584.
Wischik, C. M., Novak, M., Thogersen, H. C., Edwards, P. C., Runswick, M. J., Jakes, R., Walker, J. E., Milstein, C., Roth, M., and Klug, A. (1988). Isolation of a fragment of tau derived from the core of the paired helical filament of Alzheimer disease. Proc Natl Acad Sci U S A 85, 4506-4510.
Sawaya et al., "Atomic Structures of Amyloid Cross-Beta Spines Reveal Varied Steric Zippers", Nature, 2007, pp. 453-457, 447.
Nelson et al., "Structure of the Cross-Beta Spine of Amyloid-Like Fibrils", Nature, 2005, pp. 773-778, 435.

(56) References Cited

OTHER PUBLICATIONS

Wiltzius et al., "Atomic Structure of the Cross-Beta Spine of Islet Amyloid Polypeptide", Protein Science, 2008, pp. 1467-1474, 17.
Wiltzius et al., "Molecular Mechasims for Protein-Encoded Inheritance", Nature Structural and Molecular Biology, published online Aug. 16, 2009.
Ivanova et al., "Molecular Basis for Insulin Fibril Assembly", PNAS, 2009, pp. 18990-18995, 106.
Teng and Eisenberg, "Short Protein Segments Can Drive a Non-Fibrillizing Protein Into the Amyloid State", Protein Engineering, Design & Selection, 2009, pp. 531-536, 22.

* cited by examiner

SEQUENCE LISTING

<160> NUMBER OF SEQ ID NOS: 13

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(6)
<223> OTHER INFORMATION: L-amino acids

<400> SEQUENCE: 1

Val Gln Ile Val Tyr Lys
1               5

<210> SEQ ID NO 2
<211> LENGTH: 6
<212> TYPE: PRT
<213> ORGANISM: Homo sapiens

<400> SEQUENCE: 2

Val Gln Ile Val Tyr Lys
1               5

<210> SEQ ID NO 3
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(6)
<223> OTHER INFORMATION: L-amino acids

<400> SEQUENCE: 3

Thr Leu Lys Ile Val Trp
1               5

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Thr Leu Lys Ile Val Trp
1               5

<210> SEQ ID NO 5
<211> LENGTH: 6
<212> TYPE: PRT
<213> ORGANISM: Homo sapiens

<400> SEQUENCE: 5

Ser Ser Thr Asn Val Gly
1               5

<210> SEQ ID NO 6
<211> LENGTH: 5
<212> TYPE: PRT

```
<213> ORGANISM: Homo sapiens

<400> SEQUENCE: 6

Lys Leu Ile Met Tyr
1               5

<210> SEQ ID NO 7
<211> LENGTH: 6
<212> TYPE: PRT
<213> ORGANISM: Homo sapiens

<400> SEQUENCE: 7

Gly Gly Val Leu Val Asn
1               5

<210> SEQ ID NO 8
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(6)
<223> OTHER INFORMATION: L-amino acids

<400> SEQUENCE: 8

Tyr Gln Arg Val Tyr Lys
1               5

<210> SEQ ID NO 9
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(6)
<223> OTHER INFORMATION: D-amino acids

<400> SEQUENCE: 9

Thr Leu Lys Ile Val Trp
1               5

<210> SEQ ID NO 10
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(6)
<223> OTHER INFORMATION: D-amino acids

<400> SEQUENCE: 10

Thr Trp Lys Leu Val Leu
1               5

<210> SEQ ID NO 11
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: misc_feature
<222> LOCATION: (1)..(6)
<223> OTHER INFORMATION: D-amino acids

<400> SEQUENCE: 11

Tyr Val Ile Ile Glu Arg
1               5

<210> SEQ ID NO 12
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(6)
<223> OTHER INFORMATION: D-amino acids

<400> SEQUENCE: 12

Asp Tyr Tyr Phe Glu Phe
1               5

<210> SEQ ID NO 13
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Leu Lys His Gln Pro Gly Gly Gly Lys Val Gln Ile Val Tyr Lys Pro
1               5                   10                  15

Val Asp Leu Ser Lys Val Thr Ser
            20
```

STRUCTURE-BASED DESIGN OF PEPTIDE INHIBITORS OF AMYLOID FIBRILLATION

This application claims the benefit of U.S. Provisional Appl. No. 61/150,475, filed Feb. 6, 2009. This provisional application is incorporated by reference in its entirety and for all purposes.

SEQUENCE LISTING

The instant application contains a Sequence Listing which has been submitted in ASCII format via EFS-Web and is hereby incorporated by reference in its entirety. Said ASCII copy, created on Mar. 30, 2012, is named 58086284.txt and is 3,256 bytes in size.

BACKGROUND OF THE INVENTION

Amyloid diseases are associated with the transformation of normally soluble proteins into amyloid fibrils, which are elongated, unbranched protein aggregates (C. M. Dobson, *Trends Biochem Sci* 24, 329 (September, 1999); J. D. Sipe, A. S. Cohen, *J Struct Biol* 130, 88 (June, 2000)). Amyloid fibrils are composed mainly of β-sheets and share common characteristics, including a cross-β x-ray diffraction pattern and characteristic staining by the dye Congo Red (P. Westermark et al., *Amyloid* 14, 179 (September, 2007)). In Alzheimer's disease patients, two distinct types of fibrillar aggregates are commonly found in brain samples: amyloid plaques comprising deposits of amyloid beta protein (Aβ) and neurofibrillary tangles consisting of the microtubule-associated protein tau (D. J. Selkoe, *Physiol Rev* 81, 741 (April, 2001)). Tau filaments bind the dye thioflavine S (ThS) and yield fluorescent signal and have a cross-beta diffraction pattern (J. Berriman et al., *Proc Natl Acad Sci USA* 100, 9034 (Jul. 22, 2003); P. Friedhoff, A. Schneider, E. M. Mandelkow, E. Mandelkow, *Biochemistry* 37, 10223 (Jul. 14, 1998)). The association of tau with several diseases including Alzheimer's disease and senile dementia makes it an important target for disrupting fibrillation (J. Avila, *FEBS Lett* 476, 89 (Jun. 30, 2000)). Though recent studies suggest that small oligomers may be the pathogenic species in amyloid disease, agents that disrupt fibril formation have been shown to reduce cytotoxicity (A. Kapurniotu, A. Schmauder, K. Tenidis, *J Mol Biol* 315, 339 (Jan. 18, 2002); M. Cruz et al., *J Pept Res* 63, 324 (March, 2004)).

Because of the association of fibrils with disease, there have been several attempts at delaying and preventing fibril formation. Other proposed strategies involve small molecules (Ferrao-Gonzales et al., 2005; Ono et al., 2004; Ono et al., 2004; Ono et al., 2002; Ono et al., 2004), peptides (Tjernberg et al., 1996), and peptide variants (Cruz et al., 2004; Doig et al., 2002; Harkany et al., 1999; Kapurniotu et al., 2002; Tatarek-Nossol et al., 2005; Tjernberg et al., 1997; Wiesehan et al., 2003). These methods include using short peptide segments from the fibrillating protein (L. O. Tjernberg et al., *J Biol Chem* 271, 8545 (Apr. 12, 1996)) and variants of these peptides. The peptide variants include N-methylated backbones (E. Hughes, R. M. Burke, A. J. Doig, *J Biol Chem* 275, 25109 (Aug. 18, 2000); A. Kapurniotu, A. Schmauder, K. Tenidis, *J Mol Biol* 315, 339 (Jan. 18, 2002); D. J. Gordon, K. L. Sciarretta, S. C. Meredith, *Biochemistry* 40, 8237 (Jul. 27, 2001)), modified N- and C-termini (M. A. Findeis et al., *Biochemistry* 38, 6791 (May 25, 1999)), and D-amino acid peptides (C. Soto, M. S. Kindy, M. Baumann, B. Frangione, *Biochem Biophys Res Commun* 226, 672 (Sep. 24, 1996)). These empirical approaches are not as yet successful.

Structure-based design of amyloid fibril inhibitors has been a challenging problem. Previous structure-based approaches to prevent fibrillation have addressed only the stabilization of the native structure (Klabunde et al., 2000; Petrassi et al., 2005; Petrassi et al., 2000). This approach is not applicable to misfolding diseases in which the proteins, including tau, are thought to lack an ordered, native structure.

There remains a need in the art for improved inhibitors of fibril formation, in particular those designed using a rational structure-based approach.

SUMMARY OF THE INVENTION

In one aspect, the invention provides methods for making inhibitory peptidic compounds that inhibit aggregation of a target polypeptide. The methods can comprise, for example, 1) identifying a zipper-forming sequence in the target polypeptide that demonstrates a tendency to aggregate into a steric zipper construct; 2) identifying a template peptide sequence comprising the zipper-forming sequence or a mirror of the zipper forming sequence; 3) designing at least one complementary peptide sequence that forms energetically favorable intermolecular interactions with the template peptide sequence; and 4) identifying a candidate inhibitory peptidic compound selected from the group consisting of the complementary sequence, a mirror of the complementary sequence, a peptide mimetic of the complementary sequence and a peptide mimetic of the mirror of the complementary sequence. The methods can also comprise, for example, synthesizing the candidate inhibitory peptidic compound, and/or screening the candidate inhibitory peptidic compound for ability to inhibit aggregation of the target polypeptide. The candidate inhibitory peptidic compound can comprise, for example, six amino acid residues. In some embodiments, the target polypeptide is tau, and the steric zipper sequence is L-VQIVYK (SEQ ID NO: 1). The candidate inhibitory peptidic compound can be a peptide having a sequence such as, for example, D-TLKIVW, D-TWKLVL, D-YVIIER and D-DYYFEF. The polypeptide can also be, for example, α-synuclein, islet amyloid polypeptide, transthyretin, beta-2-microglobulin, PrP, lysozyme, huntington protein, SEVI or antibody light chain. In some embodiments, the steric zipper construct has a top and a bottom, and the candidate inhibitory peptidic compound binds preferentially to the top of the steric zipper construct. In some embodiments, the candidate inhibitory peptidic compound binds preferentially to the bottom of the steric zipper construct. The invention can also provide inhibitory peptidic compounds identified according to the screening methods disclosed herein.

In another aspect, the invention provides compounds. For example, the compounds can be peptidic compounds that inhibit aggregation of a target polypeptide. In some embodiments, the target polypeptide comprises a zipper sequence, and the peptidic compound comprising a binding moiety that binds to the zipper sequence and an inhibitory moiety that reduces aggregation of the target polypeptide. The peptidic compound can comprise, for example, one or more D-amino acid residues. In some embodiments, the polypeptide is tau and the peptidic compound can be one or more of D-TLKIVW, D-TWKLVL, D-YVIIER and D-DYYFEF.

In still another aspect, the invention provides compositions. In some embodiments, the compositions are pharmaceutical compositions comprising at least one peptidic compound disclosed herein and a pharmaceutically acceptable excipient. The excipient can be, for example, an agent that increases membrane permeability to peptides.

In yet another aspect, the invention provides methods for determining the ability of a compound to inhibit fibrillation of a target polypeptide, wherein the target polypeptide comprises a zipper-forming sequence susceptible to fibrillation. The methods can comprise, for example, 1) combining a peptidic compound of claim 12 with the target polypeptide; 2) measuring the degree of target polypeptide fibrillation; and 3) comparing the degree of target polypeptide fibrillation to a control. In some embodiments, the target polypeptide is tau protein.

In still another aspect, the invention provides methods for treating a polypeptide aggregation-associated condition in a patient in need thereof. In some embodiments, the methods comprise administering a composition comprising a compound disclosed herein to the patient, thereby treating the fibrillation-associated condition. The condition can be, for example, associated with tau protein fibrillation. The condition can be, for example, Alzheimer's disease.

BRIEF DESCRIPTION OF THE DRAWINGS

FIG. 1 discloses SEQ ID NO: 13.

FIG. 4 demonstrates the effect of amino acid residue sequence and stereochemistry, as well as the specificity of the inhibitory peptide for a particular fibril-forming polypeptide.

In FIG. 6(a), D-DYYFEF, the weakest inhibitor studied, still shows some effect at delaying fibrillation in this experiment. D-YVIIER shows clear ratio dependence in FIG. 6(b). Similar to D-TLKIVW, at 5-fold excess molar concentration, some of the 8 replicates tested of D-TWKLVL still were inhibiting fibrillation of K12, giving rise to the large error bars shown in FIG. 6(c). The inset shows the lag times for the samples at lower D-peptide concentrations.

In FIG. 7(a), the D-amino acid peptide D-TLKIVW (medium gray, translucent space-fill representation, top) was designed to pack against the top of the VQIVYK (SEQ ID NO: 2) fibril-like structure (PDB ID: 2ON9). The two β-sheets that comprise the steric zipper motif of VQIVYK (SEQ ID NO: 2) (stick representation) both interact with the D-peptide inhibitor. In FIG. 7(b), looking down the fibril axis of the packing of D-TLKIVW shows the D-peptide interacting with the top of the fibril. In FIG. 7(c), the D-amino acid peptide D-TWKLVL (medium gray) was designed to pack against the top of the VQIVYK (SEQ ID NO: 2) fibril structure. The interactions were optimized between the D-peptide and the light grey β-sheet. The top dark gray β-strand was removed in this design template. In FIG. 7(d), rotating the complex between D-TWKLVL and L-VQIVYK (SEQ ID NO: 1) to look down the fibril axis gives a top view of the predicted interaction between D-TWKLVL and L-VQIVYK (SEQ ID NO: 1). This view shows that the Trp residue in the second position of the D-peptide interacts across the β-sheet and interacts with the top β-strand and other hydrophobic interactions that bring the peptides together.

In FIG. 8(a), the D-amino acid peptide D-DYYFEF (in medium gray) was designed to pack against the bottom of the VQIVYK atomic structure. The interactions were designed to occur between the D-peptide and both (β-sheets in the structure. In FIG. 8(b), this view looks up the fibril axis of the VQIVYK fibril-like structure complexed with the peptide D-DYYFEF. The bulky, aromatic residues of D-DYYFEF were designed to prevent further propagation of the self-association of the VQIVYK segments. In FIG. 8(c), the D-amino acid peptide D-YVIIER (medium gray) was designed to pack against the bottom of the VQIVYK fibril structure. The interactions were designed to occur between the D-peptide and the light gray β-sheet shown on the right side of the figure. Interactions across to the darker gray (β-sheet shown on the left side of the figure prevent or inhibit growth of the tau fibrils. In FIG. 8(d), this view looks up the fibril axis of the VQIVYK fibril-like structure complexed with the peptide D-YVIIER. The presence of the terminal Arg residue was designed to provide charge and aliphatic bulk to disrupt the interaction between VQIVYK segments of tau. The negatively charged Glu residue makes a favorable interaction with the Lys in the VQIVYK segment.

In FIGS. 9(a) and (b), K12 is incubated alone and unbranched regular fibrils are observed by electron microscopy (scale bar represents 400 nm). In FIGS. 9(c) and (d), K12 is incubated with the peptide D-TLKIVW and small spherical particles and small irregular particles are observed, but fibrils do not form regardless of the presence of ThS. In FIGS. 9(e) and (f), K12 is incubated with the peptide D-TWKLVL. Fibrils do not form, whether in the presence or absence of ThS.

FIG. 10 depicts the sequence specificity in K12 fibrillation inhibition. The plots in this figure show the effect of other peptides incubated with K12 at equimolar ratios. FIG. 10(a) discloses "L-VQIVYK" as SEQ ID NO: 1. FIG. 10(b) discloses "L-TLKIVW" as SEQ ID NO: 3.

DETAILED DESCRIPTION

Figure 1:
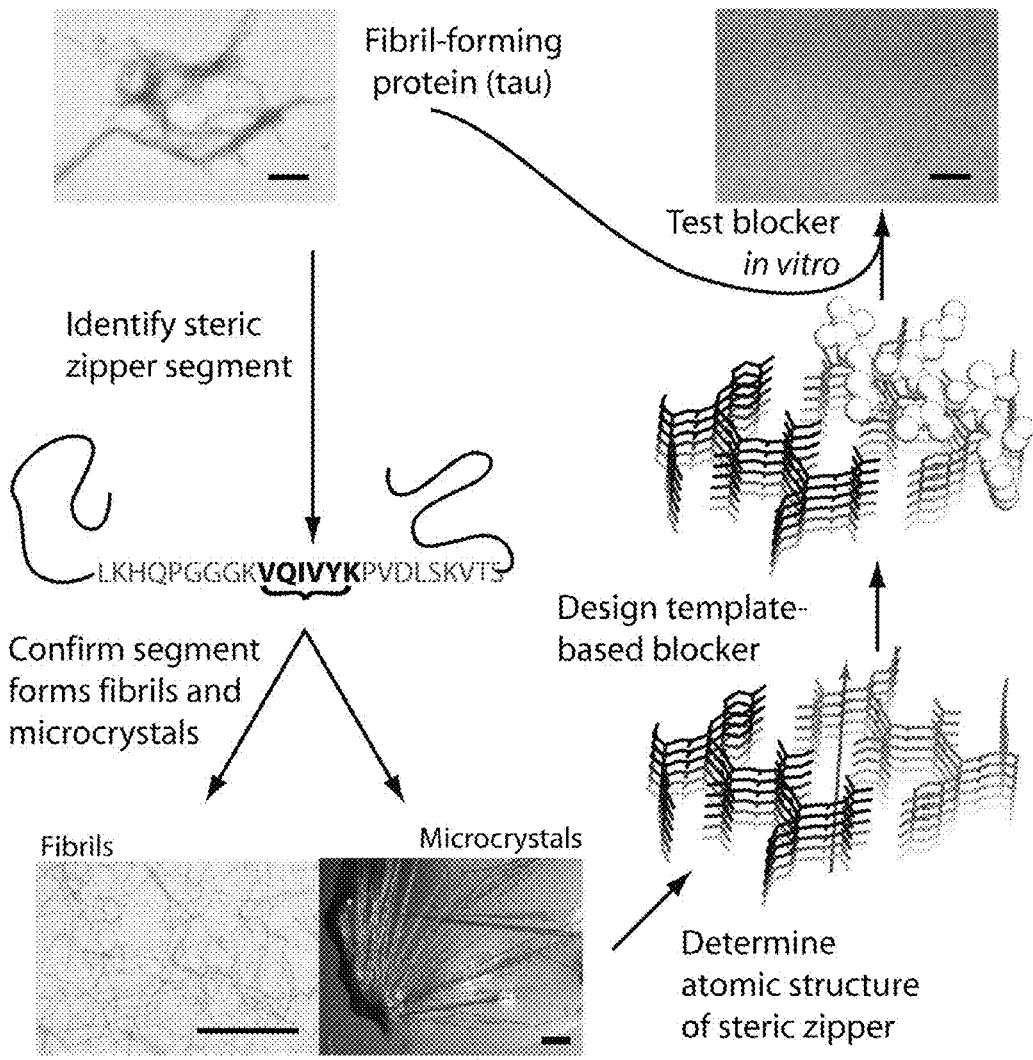
FIG. 1 is a flow chart of D-peptide design and assay. The tau construct K12 forms fibrils in vitro as seen in the electron micrograph at the top left (all electron micrographs have scale bars of 400 nm). Biochemical characterization has determined that the segment VQIVYK (SEQ ID NO: 2) is important for tau fibrillation (middle left). This segment forms fibrils and microcrystals (bottom left, scale bar of microcrystals is 100 µm). The atomic structure of the VQIVYK (SEQ ID NO: 2) segment represents a characteristic steric zipper motif. The structure comprises a pair of beta sheets. The two sheets stack into the page and interact with each other across a close hydrophobic interface. Using the structure of the segment as a template, the ROSETTADESIGN algorithm was used to design a D-amino acid peptide that would interact favorably with the structure and prevent fibril growth (middle right panel). The D-peptide satisfies hydrogen bonds and also makes favorable hydrophobic interactions with the molecule below. However, it also prevents the addition of other molecules on the opposite beta sheet. As shown in vitro, the designed D-peptide can prevent the formation of fibrils when incubated with K12. The micrograph in the upper right was taken after 14 hours.
Figure 2:
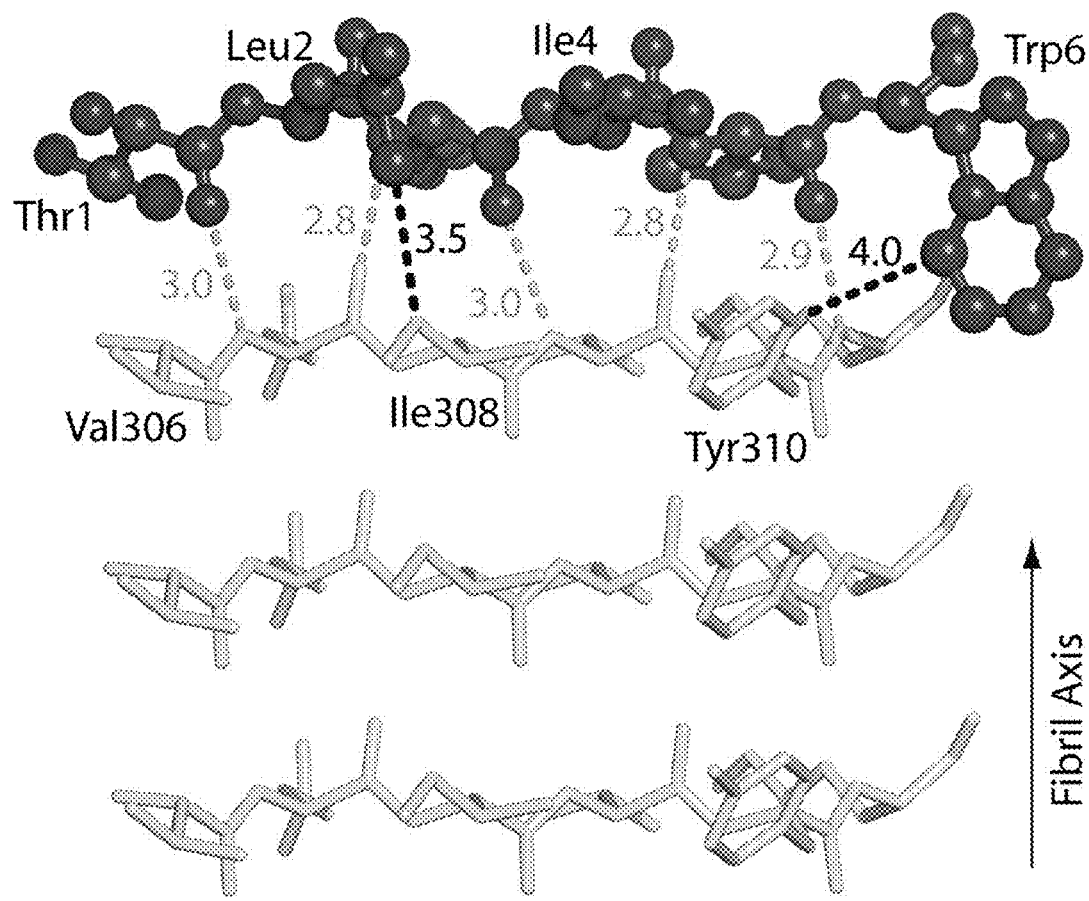
FIG. 2 is a model of the interactions between D-TLKIVW and VQIVYK (SEQ ID NO: 2). The interaction of D-TLKIVW (ball-and-stick representation) and VQIVYK (SEQ ID NO: 2 molecule (sticks) maintains all of the main chain hydrogen bonding observed in the crystal structure of VQIVYK (SEQ ID NO: 2). One hydrogen bond is lost from the stacking of glutamine residues and aromatic stacking is disrupted. However, new hydrophic interactions are predicted and the tryptophan residue of the D-peptide can interact with the tyrosine residue of the tau segment.
Figure 3A:
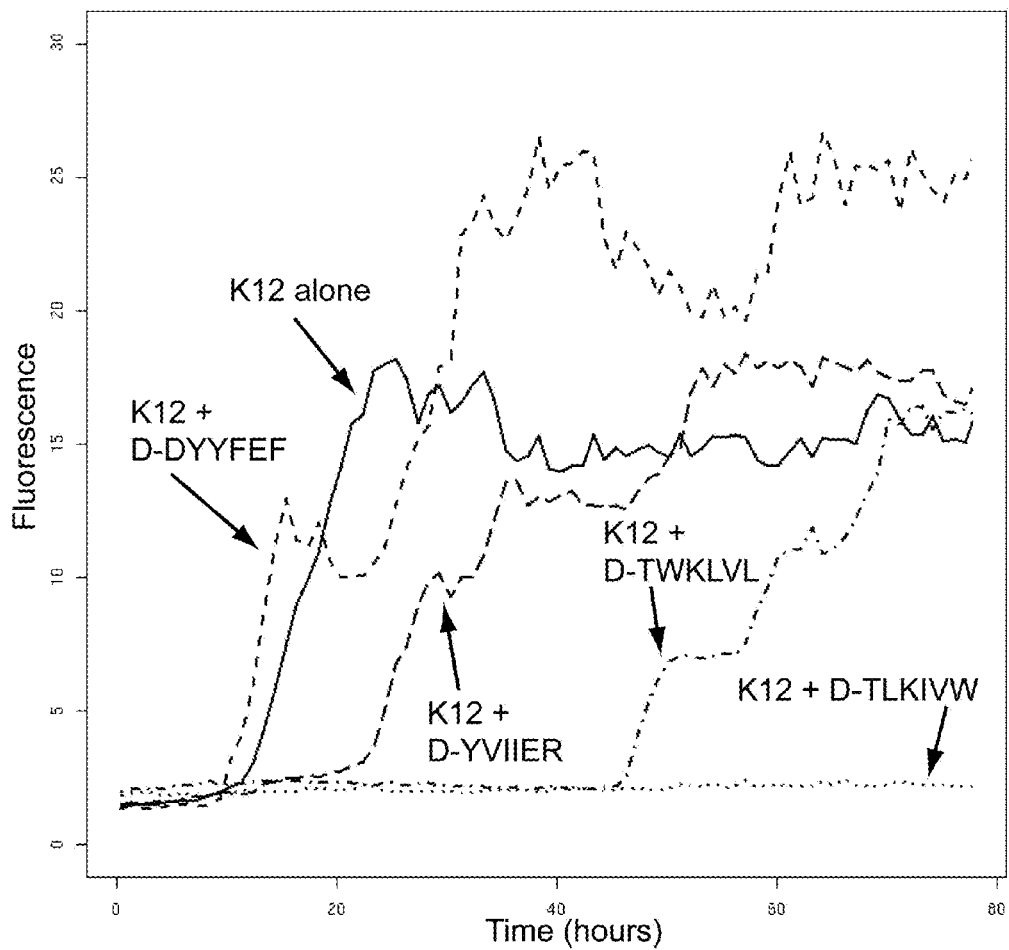
FIG. 3(a) is a plot of fluorescence as a function of time. Tau fibrillation was monitored by the fluorescence of ThS (ex. 440, em. 510). The tau K12 construct forms fibrils after about 10 hours in this assay. Incubating tau with equimolar ratios of four different designed fibril inhibiting D-peptides results in no inhibition with D-DYYFEF, some delay with D-YVIIER, a delay of more than 30 hours with D-TWKLVL, and inhibition for several days when co-incubated with D-TLKIVW.
Figure 3B:
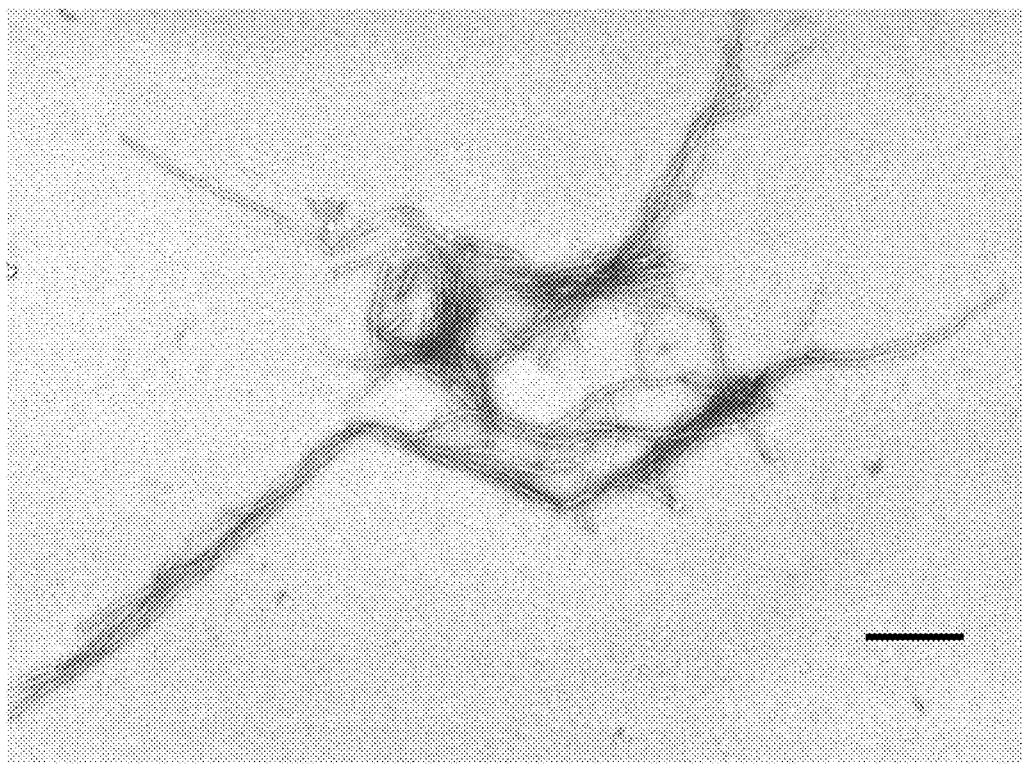
In FIGS. 3(b) and (c), electron micrographs show that the K12 construct forms fibrils (b), but incubation with equimolar amounts of the peptide D-TLKIVW prevents fibril formation (c). Scale bars represent 400 nm.
Figure 3C:
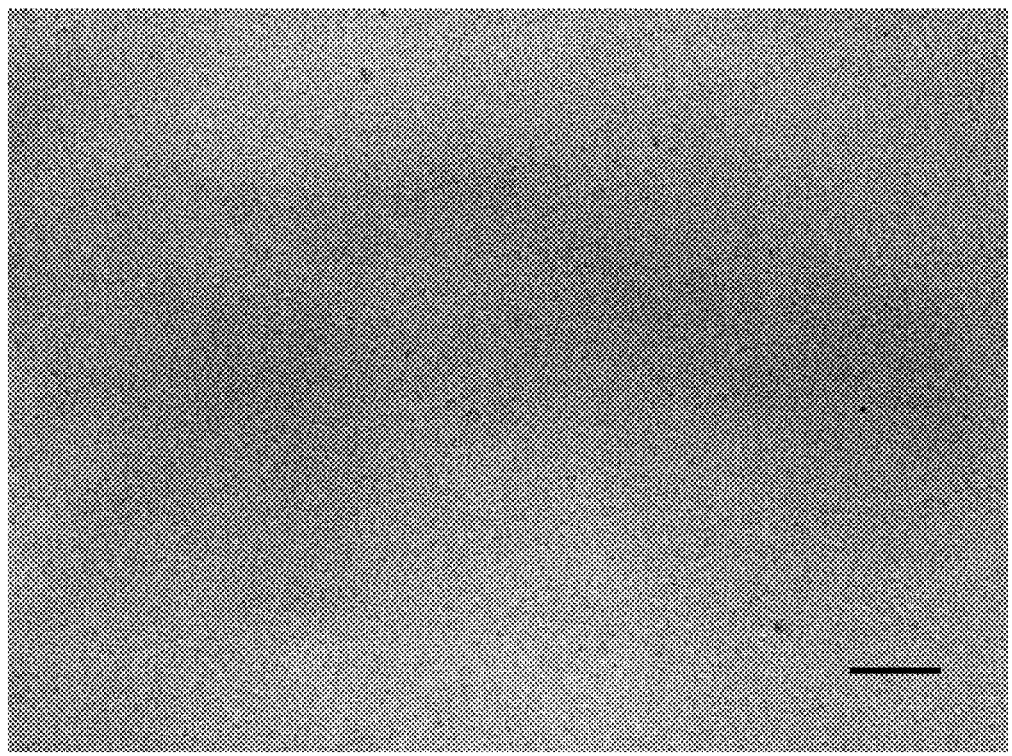
FIG. 3 depicts the effects of inhibitory D-peptides on tau fibrillation.

Embodiments of the invention are discussed in detail below. In describing embodiments, specific terminology is employed for the sake of clarity. However, the invention is not intended to be limited to the specific terminology so selected. A person skilled in the relevant art will recognize that other equivalent parts can be employed and other methods developed without parting from the spirit and scope of the invention. All references cited herein are incorporated by reference as if each had been individually incorporated.

As used herein, "peptidic compound" encompasses peptides, including, without limitation, those of up to 4, 5, 6, 7 or more amino acid residues in length, and also includes amino acid residues with D or L stereochemistry, and longer peptides and related compounds whose structure and binding capacity serve to inhibit fibril formation. "Peptidic compound" also encompasses peptidomimetic compounds. As used herein, "peptidomimetic," also referred to as "peptide mimetic," means any compound containing non-peptidic structural elements that is capable of mimicking the biochemical and/or biological action(s) of a natural mimicked peptide, including, for example, those designed to mimic the structure and/or binding activity (such as, for example, hydrogen bonds and hydrophobic packing interactions) of the peptides according to the methods disclosed herein. The zipper-binding region of the mimetic can comprise amino acid residues, whether D- or L-, whether natural or non-naturally occurring, and it can also comprise non-amino acid moieties. Peptidic compounds of the invention are those with a moiety whose structure and binding capacity enables it to inhibit fibril formation generally found in neural and/or systemic disorders characterized by fibril formation, such as those involving tau protein. From an inhibitory peptidic compound according to the invention, a person of ordinary skill using molecular modeling tools can design a peptide mimetic having the biochemical structure and/or binding activity (such as, for example, hydrogen bonds and hydrophobic packing interactions) of the inhibitory peptide, that is, it binds to the steric zipper region to inhibit fibrillation, in vivo and in vitro.

As used herein, "aggregation" means the collection and association of peptide moieties, whether the resulting structure is regular or irregular, repeating or non-repeating, stable or unstable or with ordered or disordered native states. Such association can occur through intermolecular interactions, ionic bonds, hydrophobic interactions, hydrogen bonds, van der Waals forces, i.e. "London dispersion forces," and dipole-dipole bonds, or any force or substance that can result in the collection or association together of two or more peptides or peptide regions. As used herein, "aggregation" encompasses, for example, fibrillation, or the formation of fibrils. "Aggregation" also encompasses the formation of a steric zipper. As used herein, a "target protein" or "target polypeptide" means any peptide structure that has a tendency to form fibrils, for example amyloid fibrils. Examples of target proteins include, without limitation, amyloid beta, tau, α-synuclein, islet amyloid polypeptide (IAPP), beta-2-microglobulin, semen-derived enhancer of viral infection (SEVI) immunoglobulin light chains, huntington protein, PrP prion protein and lysozyme. As used herein, "aggregation" encompasses "fibrillation."

As used herein, "steric zipper region," also referred to as a "steric zipper sequence" or "zipper-forming sequence," means a sequence of amino acid residues in an aggregating polypeptide, such as a fibril-forming polypeptide, that interacts with similar sequences on other polypeptides to form steric zipper constructs such as, for example, fibrils. In one example, a steric zipper region can involve an amino acid sequence in a β sheet which is capable of interdigitating with its neighboring β-sheet across an interface, often with a similar amino acid sequence on the neighboring β-sheet. Such interdigitation can occur through, for example, the side chains of the amino acid residues.

As used herein, "energetically favorable intermolecular interactions" can include, for example, both covalent and non-covalent interatomic and intermolecular interactions. Examples include, without limitation, ionic bonds, hydrophobic interactions, hydrogen bonds, Van der Waals forces, i.e. "London dispersion forces," and dipole-dipole bonds.

As used herein, "screening test" encompasses tests conducted to determine if candidate inhibitory peptides are effective in disrupting fibril formation. Examples of such screening tests are described herein. However, a person of ordinary skill would recognize that other screening tests can be employed without departing from the spirit and scope of the invention.

As used herein, "disrupt," in the context of fibril formation, can include preventing, reducing, inhibiting or slowing the rate of increase of fibril formation, in vitro or in vivo, in a cell-free system, a cell culture, in tissue, or in an organism, including an animal such as a human or other mammal.

"Amyloidosis," as used herein, encompasses a variety of conditions in which amyloid proteins are abnormally deposited in organs and/or tissues. A protein is described as being amyloid if, due for example to an alteration in its secondary structure, it takes on an aggregated insoluble form similar to the beta-pleated sheet. Examples of conditions involving amyloidosis include, for example, Alzheimer's disease; Parkinson's disease (α-synuclein amyloidosis); amyotrophic lateral sclerosis (commonly known as Lou Gehrig's disease); type II diabetes (islet amyloid polypeptide (IAPP) amyloidosis); lysozyme amyloidosis; disorders associated with amyloid formation involving transthyretin fibrillation, such as, for example, familial and senile amyloidosis; prion diseases (CVJ, vCJD, GSS); cardiac amyloidosis; HIV sexual transmission associated with the SEVI form of prostate activating protein of semen and antibody light chain amyloidosis affecting kidney function.

As used herein, a "mirror peptide" means a peptide in which the amino acid sequence is the same as that of a reference peptide, but in which each amino acid has the opposite stereochemistry. For example, a sequence made up of the L stereoisomers of "VQIVYK" (SEQ ID NO: 2) would have a mirror peptide with the same amino acid sequence—i.e., VQIVYK (SEQ ID NO: 2)—but in which each alpha carbon has D stereochemistry. A mirror peptide can include natural or non-naturally-occurring amino acids or other chemical entities, for example those that can mimic peptide chemistry, and can include all L-residues or all D-residues.

As used herein, "complementary," when used in reference to peptide sequences, means a sequence that interacts favorably with another peptide sequence of interest. A complementary sequence can include natural or non-naturally-occurring amino acid residues, and such sequence can be made up of all L-residues or all D-residues. A complementary peptide sequence can be designed, for example, with the aid of modeling software, such as the RosettaDesign software, to form energetically favorable interactions with another compound, such as, for example, a peptide sequence such as a template peptide sequence. A complementary peptide sequence can be, for example, a rotamer, such as an L-rotamer. Consequently, a person or ordinary skill would appreciate that the term "rotamer" can be substituted with "complementary peptide sequence" wherever it appears herein.

A "template peptide sequence," as used herein, means a sequence that is used as the basis for the design of another peptide sequence, such as, for example, a complementary peptide sequence. A template peptide sequence can be a steric zipper sequence, a mirror of a steric zipper sequence, or another construct that can be used in the design of a complementary peptide sequence.

As used herein, "bind" encompasses both covalent and non-covalent interatomic and intermolecular interactions, whether long lasting or transient. Examples include, without limitation, ionic bonds, hydrophobic interactions, hydrogen bonds, Van der Waals forces, i.e. "London dispersion forces," and dipole-dipole bonds.

"Polypeptide aggregation-associated condition," as used herein, means conditions characterized by the aggregation of polypeptides of a kind, or to a degree, that is not commonly observed in healthy subjects. Examples of such conditions include, for example, Alzheimer's disease; Parkinson's disease (α-synuclein amyloidosis); amyotrophic lateral sclerosis (commonly known as Lou Gehrig's disease); type II diabetes (islet amyloid polypeptide (IAPP) amyloidosis); lysozyme amyloidosis; disorders associated with amyloid formation involving transthyretin fibrillation, such as, for example, familial and senile amyloidosis; prion diseases (CVJ, vCJD, GSS); cardiac amyloidosis; HIV sexual transmission associated with the SEVI form of prostate activating protein of semen and antibody light chain amyloidosis affecting kidney function. As used herein, "target polypeptide" encompasses, for example, whole, native polypeptides with a feature that favors aggregation, such as a zipper-forming sequence; partial polypeptides that retain the aggregation-favoring feature; or mimetics that include the aggregation-favoring feature but that also include non-peptide structural elements.

The invention provides methods for designing peptidic compounds (including peptides and peptidomimetics) that inhibit fibrillation in target proteins (polypeptides) that have a tendency to form fibrils. The methods can involve the following steps:

1) identifying a target protein that has a tendency to form fibrils;

2) identifying the amino acid sequence of the steric zipper region on the fibril-forming protein;

3) designing a peptide sequence comprising the same amino acids as the steric zipper region, only with the opposite stereochemistry—i.e., the D-enantiomer rather than the L-enantiomer;

4) designing a set of L-rotamers from a library of L-amino acids (both natural and unnatural/synthetic) that form energetically favorable intermolecular interactions with the D-amino acid sequence, and also possess a zipper-disrupting feature;

5) preparing a candidate inhibitory peptide having an oligomeric amino acid sequence comprising the same amino acids as the L-rotamers, but having the opposite stereochemistry, and 6) screening the candidate inhibitory peptides for inhibition of fibrillation in the target protein.

The candidate inhibitory peptides have an oligomeric sequence that forms energetically-favorable interactions with the amino acid sequence of the steric zipper region of the target protein, and also possess a zipper-disrupting feature that disrupts the peptide stacking at the steric zipper region.

This method can be used to obtain inhibitory peptides to disrupt fibril formation involving any protein for which a steric zipper sequence can be identified. For example, it is effective in designing fibril-inhibiting peptides for the following target proteins involved with amyloidosis: tau protein, associated with amylodosis in Alzheimer's disease; α-synuclein, associated with amyloidosis in Parkinson's disease; islet amyloid polypeptide, associated with amyloidosis in type II diabetes; and also lysozyme amyloidosis; transthyretin amyloidosis; and amyloidosis affecting kidney function.

The invention also provides fibrillation-inhibitory peptides. For example, fibrillation-inhibitory peptides associated with tau fibrillation include D-TLKIVW, D-TWKLVL, D-YVIIER and D-DYYFEF. Each of these peptides binds to the tau fibrils, generally at the steric zipper region, which comprises the amino acid residues L-VQIVYK (SEQ ID NO: 1). The inhibitory peptides include a zipper-inhibitory feature comprising side chains that project out from the inhibitory peptide sequence backbone in such a way as to interfere with binding of subsequent zipper sequences to the nascent fibril.

The inhibitory peptides of the invention may be used in methods of treating fibrillation-associated diseases. The invention provides pharmaceutical compositions useful for treating fibrillation-associated diseases. The pharmaceutical composition comprises a fibrillation-inhibitory peptide and a pharmaceutically acceptable excipient. Suitable excipients for use with these compositions can assist the inhibitory peptide in crossing physiological barriers, such as the blood-brain barrier.

The methods disclosed herein can be used, for example, to design peptides that recognize amyloid and other peptides with steric zipper regions in vivo. Such methods can be used to aid in diagnosing amyloidosis, where specific binding is achieved. Specific recognition of the formation of a steric zipper by a small molecule with an entity such as a dye or a radiolabeled moiety attached can be detected. Such a method can be useful for early detection of tangles and other fibril aggregates.

In some embodiments, the invention provides methods for designing D-amino acid fibril-capping peptides. These methods can involve, for example, creating a novel interface between the inhibitor molecule and a steric zipper segment structure. For example, starting with the atomic-level structure of the VQIVYK (SEQ ID NO: 2) segment from tau, a D-amino acid fibril blocker is designed. The blocker is designed to interact favorably with its fibril-like scaffold, but also to project side chains away from the scaffold to prevent the addition of molecules to the fibril spine. Effective blocking strategies can involve other mechanisms as well. For example, inhibitors can be designed that alter the tertiary structure of the zipper region such that it no longer lines up properly with another zipper region; permanently modifying steric zipper or inhibitory peptide side chains after a specific recognition, or covalent modifications that add bulk to steric zipper core. ThS fluorescence assays and electron microscopy can be used to show that these D-amino acid peptides inhibit fibril formation (FIG. 1). This structure-based approach can be used to design inhibitors of fibrils formed by other proteins if the structure of fibril-forming segments is known or can be accurately predicted, which can lead to the design of therapeutics for fibril-forming diseases.

The methods disclosed herein can be used to design inhibitory peptides of various types and conformations. For example, the method can start with an L-zipper sequence and can then include using a template sequence that is composed of a sequence of D-residues. The D-residue template can then be used to design an L-residue complementary sequence, which is in turn used to identify a D-residue candidate inhibitory peptide. Similarly, an L-zipper sequence can itself serve as the template sequence, which can be used to design an L-residue complementary sequence, which is itself a candidate inhibitory peptide. A complement comprising a combination of L- or D-residues can be designed from either an L or a D template sequence. And a complement comprising a combination of L- or D-residues can be used in the identification of a candidate inhibitory peptide that is either the complement itself, the minor of the complement, or a mimetic of either the complement or the minor of the complement. The zipper-binding region of the mimetic can comprise amino acid residues, whether D- or L-, whether natural or non-naturally occurring, and it can also comprise non-amino acid moieties.

In one aspect, the invention provides methods for making inhibitory peptides and peptidic compounds. These inhibitory peptides and peptidic compounds can, for example, inhibit aggregation of target polypeptides into fibrils. These methods can comprise the steps of: 1) identifying a zipper-forming sequence in the target polypeptide that demonstrates a tendency to aggregate into a steric zipper construct; 2) preparing a mirror peptide comprising the D-enantiomers of the L-amino acid residues in the zipper-forming sequence; 3) designing a plurality of L-rotamers that form energetically favorable intermolecular interactions with the mirror sequence; 4) identifying a candidate inhibitory peptide comprising a D-enantiomer of the amino acid residues of a target L-rotamer, and 5) screening the candidate inhibitory peptide for ability to inhibit aggregation of the target polypeptide into fibrils. In some embodiments, the target polypeptide is tau, and the steric zipper sequence is L-VQIVYK (SEQ ID NO: 1). The candidate inhibitory peptide sequence can be, for example, one or more of D-TLKIVW, D-TWKLVL, D-YVIIER and D-DYYFEF. The target polypeptide can also be, for example, α-synuclein, islet amyloid polypepdite, transthyretin, beta-2-microglobulin, semen-derived enhancer of viral infection (SEVI), prion protein (PrP), lysozyme, huntington protein or antibody light chain.

In still another aspect, the invention provides methods for decreasing polypeptide fibrillation in a composition, wherein the composition comprising a target polypeptide susceptible to fibrillation. The methods can comprise, for example introducing into the composition one or more of the peptidic compounds disclosed herein, thereby decreasing polypeptide fibrillation. In some embodiments, the target polypeptide is tau protein. In some embodiments, the invention provides methods for treating a polypeptide fibrillation-associated condition in a patient in need thereof. These methods can comprise, for example, administering a composition comprising one or more of the peptidic compounds disclosed herein to the patient, thereby treating the fibrillation-associated condition. The condition can be, for example, associated with tau protein fibrillation. The condition can be, for example, Alzheimer's disease.

D-amino acid peptides can be designed to cap the ends of the structure of the VQIVYK steric zipper. These peptides can inhibit the formation of aggregates in target proteins such as tau. To design a protease-resistant inhibitor, the methods can involve, for example, reversing the stereochemistry of the steric zipper structure (which is built from L-amino acids) to create a virtual D-amino acid structure of the steric zipper. Because of the polarity of the fibril axis found in the steric zipper structure, peptide inhibitors or caps can be designed for both the top and bottom of the steric zipper. The Rosetta-Design algorithm (available at <http//rosettadesign.med.unc.edu/>; licensing terms can be found at <http://depts-.washington.edu/ventures/UWTechnology/Express Licensees/rosetta.php>) can be used to build a set of L-rotamers and selected those that would favorably interact with the D-amino acid steric zipper (B. Kuhlman et al., *Science* 302, 1364 (Nov. 21, 2003)). The procedure can include using RosettaDesign to select from a library of all L-amino acid rotamers, and is not limited to natural amino acids. Appropriate rotamers are selected to optimize packing against the D-amino fibril template. Successive rounds of design are performed by a researcher, who limits the rotamer search to ignore undesired amino acids, i.e., those that lack favorable packing and interaction features. This involves evaluating candidate peptides for interaction energy and favorable packing by visual inspection and through features including, for example, area buried and shape complementarity. Candidate inhibitors are selected from the entire space of peptides of the length desired. After the computational design of the L-amino acid inhibitor peptides against the D-amino acid steric zipper, the virtual stereochemistry is reversed to synthesize D-amino acid fibril blockers of the L-amino acid steric zipper.

According to the methods disclosed herein, with the knowledge of the structures of steric zippers involved in amyloid fibrils, inhibitors can be designed for disordered proteins as well as those with ordered native states. Atomic-level structures of short fibril-forming segments provide structural templates for rational peptide inhibitor design. Combining knowledge of these structures with techniques to design novel proteins and protein-protein interfaces, inhibitors can be developed that interact with the fibril-like structure of the segment VQIVYK (SEQ ID NO: 2) from tau. Steric zipper structures provide important information about the interactions between molecules in a fibril, and, according to the methods disclosed herein, can be used in a general approach for creating fibril blockers for any fibril-forming protein. According to the methods disclosed herein, D-amino acid peptides can be designed to inhibit fibrillation using the structure of a small segment from an amyloidogenic protein.

In some embodiments, the invention provides a computational strategy for the design of D-amino acid peptides that inhibit the formation of amyloid fibrils using the atomic structures of segments, which form the spines of amyloid fibrils. Using the methods disclosed herein, D-amino acid peptides can be designed that optimize packing interactions with the fibril spine structure, but prevent fibril elongation. For example, a D-peptide designed to block elongation of the segment VQIVYK (SEQ ID NO: 2) inhibits fibril formation of a 13 kD tau construct containing this segment. The β-sheet spine structures of short segments from amyloid fibril-forming proteins provide insight into the nature of interactions between proteins in fibrillar form, indicating that the methods disclosed herein for designing peptides that block amyloid fibrillation may be general. It would apply, for example, to Alzheimer's disease, Parkinson's disease (α-synuclein amyloidosis), amyotrophic lateral sclerosis (commonly known as Lou Gehrig's disease), type II diabetes (islet amyloid polypeptide (IAPP) amyloidosis), lysozyme amyloidosis, as well as disorders associated with amyloid formation involving transthyretin and amyloidosis affecting kidney function (beta-2-microglobulin amyloidosis). Inhibitors designed to the SSTNVG (SEQ ID NO: 5) segment of islet amyloid polypeptide (IAPP, also known as amylin) can combat diabetes type 2. Inhibitors designed to the KLIMY (SEQ ID NO: 6) and GGVLVN (SEQ ID NO: 7) segments of SEVI can interfere with HIV sexual transmission.

In some embodiments, the invention provides methods for determining the ability of a compound to inhibit fibrillation of a target polypeptide, wherein the target polypeptide comprises a zipper-forming sequence susceptible to fibrillation. These methods can comprise, for example, combining a peptidic compound disclosed herein with the target polypeptide; measuring the degree of target polypeptide fibrillation; and comparing to a control. The combining step can be carried out in any suitable medium or under any suitable reaction conditions, including, for example, in solution, on a surface, in vitro, in a cell culture, in tissue culture, or in vivo.

The compositions of the present invention can be administered to any mammal in need of the composition that can experience the beneficial effects of the compounds of the invention. Any such mammal is considered a "patient." Such patients include humans and non-humans, such as pets and farm animals.

In another aspect, the invention provides compounds. The compounds can be, for example, peptidic compounds that inhibit aggregation of a target polypeptide. In some embodiments, the target polypeptide comprises a zipper sequence and the peptidic compound comprises a binding moiety that binds to the zipper sequence and an inhibitory moiety that reduces aggregation of the target polypeptide into amyloid fibrils. A "binding moiety" can be a region of the peptidic compound that undergoes favorable energetic interactions with the target polypeptide, for example at its zipper sequence. A peptidic compound can comprise more than one binding moieties. An "inhibitory moiety" can be a region of the peptidic compound that reduces, alters, interferes with or inhibits the aggregation of target polypeptides, for example at their zipper regions, via any of the mechanisms disclosed herein. The peptidic compound can comprise, for example, one or more D-amino acid residues. In some embodiments, the polypeptide is tau and the peptidic compound is one or more of D-TLKIVW, D-TWKLVL, D-YVIIER and D-DYYFEF.

Using the atomic level structures of amyloid-like peptides, a method has been developed to predict, for example, D-amino acid peptide inhibitors of amyloid fibril formation. The method can be used to develop peptides comprising different D-amino acids such that the peptides reduce, inhibit or prevent the formation of tau fibrils commonly found in intracellular paired helical filaments in the brains of Alzheimer's disease patients. The methods disclosed herein can be applied to systems in which fibrils are formed. The use of structural information allows for the design of potent inhibitors to many fibril-forming proteins. For example, peptides have been developed that can inhibit fibrillation of the K12 construct of tau in vitro. Because fibril formation is associated with disease, and because fibrils and smaller oligomers can lead to cell toxicity, these peptides can be useful in pharmaceutical preparations to treat these diseases. The methods disclosed herein can use non-natural amino acids as well as naturally-occurring ones. In addition, the steric zipper structures can be used to evaluate peptide mimetics that mimic the hydrogen bonding patterns and hydrophobic interactions of the blocking peptides.

The determination of structures of several short segments from proteins that form amyloid-like fibrils, including VQIVYK (SEQ ID NO: 2) from tau, has led to the determination of the molecular basis for shared features observed in amyloid-like fibrils. The shared structural feature of all these segments, termed a steric zipper, contains a pair of β-sheets, in which the amino acid side chains from one β-sheet interdigitate with its neighboring β-sheet across an interface that excludes all solvent. These segment structures can contain molecular features that are important for the fibrillation of its parent protein. Accordingly, disrupting packing of the segment structure can lead to disrupting the fibrillation of the full-length protein.

D-amino acid peptides and peptide mimetics can be used as protease-resistant alternatives to effective L-amino acid peptides. By designing D-peptides to the fibril template according to the methods disclosed herein, it is possible to create effective inhibitor peptides unrelated in sequence to the target self-associating steric zipper. The methods disclosed herein enable the rational design of inhibitor molecules that can interact with a fibril core and are resistant to protease degradation. Peptide fibril inhibitors can be effective at reducing cytotoxicity both in cell cultures and in in vivo models.

According to the invention, there are similar underlying atomic interactions between molecules in a fibril and in small oligomers. Hence, disrupting the interactions of a β-sheet fibril spine can be an effective approach to disrupting cytotoxicity. Peptides can cross the blood brain barrier and prevent cytotoxicity, for example in a rat model (Soto et al., 1998). The combination of design strategies for blocking fibrillation and strategies for increasing the permeability of peptides across membranes is helpful in testing fibril blockers for efficacy as therapeutic molecules. Cell-based assays can be used to determine the cytotoxicity of D-TLKIVW and its effectiveness in disrupting tau fibrillation in vivo. Peptides that inhibit fibril formation increase understanding of the important molecular interactions between molecules in amyloid fibrils and lead to successful therapeutics according to the methods disclosed herein for preventing aggregation of proteins associated with amyloid and other diseases involving fibrillation. Because smaller molecules are often easier to deliver to affected tissues than are peptides, the invention encompasses using understanding of structural features to move toward smaller peptides and peptidomimetics that replicate the features that help in preventing, inhibiting or reducing fibrillation. Designing peptide molecules and using peptide adaptations for increasing membrane permeability enables the creation new lead therapeutics for delaying the onset of several diseases. The similarities and differences in amyloid-like fibers from several proteins suggest that the methods described herein can be applied to any system with a known steric zipper structure to create specific inhibitors of fibrillation.

Several diseases, including type II diabetes, Parkinson's disease and Alzheimer's disease, are associated with the transformation of normally soluble proteins into amyloid fibrils: elongated, unbranched protein aggregates (Dobson, 1999; Sipe and Cohen, 2000). In Alzheimer's disease patients, two distinct types of fibrillar aggregates are commonly found in brain samples: amyloid plaques comprising deposits of amyloid beta protein (Aβ) and neurofibrillary tangles consisting of the microtubule-associated protein tau (Selkoe, 2001). Aβ aggregates are mainly β-sheets with all the hallmark characteristics of amyloid fibrils, including a cross-beta diffraction pattern and characteristic staining by the dyes Congo Red and thioflavin T (Eanes and Glenner, 1968; LeVine, 1993; Sipe and Cohen, 2000). Tau filaments adopt various morphologies, including paired helical filaments (PHFs), which are β-sheet rich fibrils that appear as twisted structures under electron microscopy, and straight filaments, which lack the twisted morphology (Goedert et al., 1998). Tau filaments bind the dye thioflavine S (ThS) and yield fluorescent signal and have a cross-beta diffraction pattern (Berriman et al., 2003; Friedhoff et al., 1998). The association of tau with several diseases including Alzheimer's disease and senile dementia makes it an important target for disrupting fibrillation.

Tau contains four microtubule-binding regions, which have been implicated in the assembly of tau filaments. These repeat domains are found in the core of PHFs from multiple tau isoforms and can assemble into PHF-like fibrils in isolation (Kondo et al., 1988; Wille et al., 1992; Wischik et al., 1988). The fibrillation of tau depends on the formation of β sheets by the short segment VQIVYK (SEQ ID NO: 2) from the third repeat and that this segment in isolation forms amyloid-like fibrils. Consequently, this segment of tau involved in the fibril spine can be used as a target for disrupting tau fibrillation. Because full-length tau isoforms are about 400 amino acids long, several smaller constructs with similar properties have been created for experimental convenience. One of these constructs, termed K12, contains three tau microtubule-binding repeats and its sequence contains residues Q244-Y394 with a starting Met residue, without the second microtubule-binding repeat V275-S305 (Schweers et al., 1995; Wille et al., 1992). This 13 kDa derivative of tau contains the VQIVYK (SEQ ID NO: 2) segment and forms PHFs in vitro (Schweers et al., 1995; Wille et al., 1992).

Structure-based design of amyloid fibril inhibitors is a challenging problem. To date, other structure-based approaches to prevent fibrillation have addressed the stabilization of the native structure (T. Klabunde et al., *Nat Struct Biol* 7, 312 (Apr. 2000); H. M. Petrassi et al., *J Am Chem Soc* 127, 6662 (May 11, 2005); H. M. Petrassi, T. Klabunde, J. Sacchettini, J. W. Kelly, *J. Am. Chem. Soc.* 122, 2178 (2000)). This approach is not as effective in misfolding diseases in which the proteins are thought to lack an ordered, native structure, examples of which include proteins involved in amyloid diseases, including tau. With the knowledge of the structures of steric zippers involved in amyloid fibrils, the methods disclosed herein can be used to design inhibitors for disordered proteins as well as those with ordered native states. Atomic-level structures of short fibril-forming segments can be used to provide structural templates for rational peptide inhibitor design. Using these structures and designing novel proteins and protein-protein interfaces, inhibitors have been created that interact with the fibril-like structure of the segment VQIVYK (SEQ ID NO: 2) from tau. Elucidation of the steric zipper structures can provide important information about the interactions between molecules in a fibril, and, according to the methods disclosed herein, can be used in a general approach for creating fibril blockers for any fibril-forming protein.

According to the disclosed methods, D-amino acid peptides can be designed to inhibit fibrillation using the structure of a small segment from an amyloidogenic protein. D-amino acid peptides can be used as protease-resistant alternatives to effective L-amino acid peptides. By designing D-peptides to the fibril template, it is possible to create effective inhibitor peptides unrelated in sequence to the target self-associating steric zipper. The L-amino acid peptide, L-TLKIVW (SEQ ID NO: 3), was able to inhibit fibril formation, but not nearly as long as D-TLKIVW (FIG. 4*c*). The methods disclosed herein enable the rational design of inhibitor molecules that interact with a fibril core and are resistant to protease degradation.

Peptide fibril inhibitors can be effective at reducing cytotoxicity both in cell cultures and in vivo systems, suggesting that there are similar underlying atomic interactions between molecules in a fibril and in some small oligomers. Hence, disrupting the interactions of a β-sheet fibril spine seems can be an effective approach to disrupting cytotoxicity. Peptides can cross the blood brain barrier and prevent cytotoxicity, as demonstrated in a rat model (C. Soto et al., *Nat Med* 4, 822 (July, 1998)). The combination of the design strategies for blocking fibrillation disclosed herein and strategies for increasing the permeability of peptides across membranes can produce fibril blockers that are useful as therapeutic molecules. Based on the similarities and differences of amyloid-like fibers from several proteins, the methods disclosed herein can be applied to any system with a steric zipper structure to create specific inhibitors of fibrillation.

The structures of several short segments from proteins that form amyloid and amyloid-like fibrils have been determined. These segment structures, including VQIVYK (SEQ ID NO:

2 from tau, reveal the molecular basis for the common features observed in amyloid-like fibrils. The main common structural feature of all these segments, termed a steric zipper, contains a pair of β-sheets, in which the amino acid side chains from one β-sheet interdigitate with its neighboring β-sheet across an interface that excludes all solvent. These segment structures contain molecular features that are important for the fibrillation of its parent protein, and disrupting packing of the segment structure can be applicable to disrupting the fibrillation of the full-length protein. The methods disclosed herein provide an approach to designing D-amino acid fibril-capping peptides, which involves creating a novel interface between the inhibitor molecule and a steric zipper segment structure. Starting with the atomic-level structure of the VQIVYK (SEQ ID NO: 2) segment from tau, a D-amino acid fibril blocker is designed which interacts favorably with its fibril-like scaffold, but also projects side chains away from the scaffold to prevent the addition of molecules to the fibril spine. ThS fluorescence assays and electron microscopy can be used to demonstrate that these D-amino acid peptides inhibit fibril formation. This structure-based approach can be used to design inhibitors of amyloid fibrils formed by other proteins if the structure of fibril-forming segments is known or can be accurately predicted.

The following table lists other peptides that can have an inhibitory effect:

| Category | Examples |
| --- | --- |
| Original designs | D-TLKIVW |
| | D-TWKLVL |
| | D-YVIIER |
| | D-DYYFEF |
| Stereoisomer | L-TLKIVW (SEQ ID NO: 3) |
| Cysteines attached to residues with a glycine linker | CGGG-D-TLKIVW |
| | D-TLKIVW-GGGC |
| Lysine substitutions | D-TLRIVW |
| | D-TL(Citrulline)IVW |
| | D-TL(Ornithine)IVW |
| | D-TLQIVW |
| | D-TLNIVW |
| | D-TLAIVW |
| | D-TLMIVW |
| Truncations | D-LKIV |
| | D-KIVW |
| | D-LKI |
| | D-KIV |
| | D-LKIVW |
| Scrambled peptides | D-TIKWVL |
| Original L-amino acid design | L-YQRVYK (SEQ ID NO: 8) |

Pharmaceutical Compositions and Administration

Dosage effect (Molar amount of peptide relative to tau K12 construct to delay fibrillation). A marginal effect was observed at a molar ratio of 50-fold less peptide relative to tau K12 concentration for D-TLKIVW and 10-fold less for D-TWKLVL. Other peptides require equimolar or excess peptide to see any inhibitory effect.

Delivery approaches can include oral ingestion, injection, or topical application. For example, in the case of SEVI, vaginal delivery can be appropriate. Preparations for delivery can include peptide alone, peptide in some lipid or protein encapsulation, in liposomes attached to a dendramer, peptide with other molecules attached to a linker. The compound can also be encapsulated according to methods known in the art, or packaged into micelles or delivered in association with nanoparticles.

The invention contemplates other options for improvement of the design using peptide mimics, blocked ends, other chemical attachments, cyclized molecules, N-methylated backbone, substitution of non-natural amino acids. We specifically studied the effect of D-TLKIVW with 3 glycine residues and cysteine at the C-terminus. This permits us to attach many other molecules (PEGs, sugars, DMSO, adding polyamines, like putrescine) that may increase cell permeability and blood-brain barrier permeability (see Soto et al's 2008 rat model study) or have other effects.

Fluorophores could potentially be attached for diagnostic purposes for example. Many other options here can be imagined, as would be appreciated by a person of ordinary skill in the art.

K12 is purified by cation exchange via method of Barghorn, S., Biernat, J., and Mandelkow, E. (2005). Purification of recombinant tau protein and preparation of Alzheimer-paired helical filaments in vitro can be accomplished according to Methods Mol Biol 299, 35-51.

Pharmaceutical compositions for use in accordance with the present invention may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

Suitable routes of administration may, for example, include intravesical, oral, rectal, vaginal, transmucosal, especially transnasal, intestinal or parenteral delivery, including intramuscular, subcutaneous and intramedullary injections as well as intrathecal, direct intraventricular, intravenous, intraperitoneal, intranasal, or intraocular injections. The pharmaceutical composition may be administered locally or systemically. For example, the composition can be administered locally via injection of the preparation directly into a specific region of a patient's body, such as for example through the urethra (for transurethral administration).

For injection, the active ingredients of the invention may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

The compositions may be formulated for intravesical administration. For such formulations, suitable vehicles can comprise saline, phosphate-buffered saline (i.e., PBS) and/or gelatin nanoparticles. Other suitable vehicles and methods of preparation will be apparent to a person of ordinary skill in the art.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The preparations described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The preparation of the present invention may also be formulated in rectal compositions such as suppositories or retention enemas, using, e.g., conventional suppository bases such as cocoa butter or other glycerides.

Pharmaceutical compositions suitable for use in context of the present invention include compositions wherein the active ingredients are contained in an amount effective to achieve the intended purpose. More specifically, a therapeutically effective amount is an amount of one or more active ingredients effective to prevent, alleviate or ameliorate symptoms of disease or prolong the survival of the subject being treated.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions including the preparation of the present invention formulated in a compatible pharmaceutical carrier may also be prepared, placed in an appropriate container, and labeled for treatment of an indicated condition.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Additional objects, advantages, and novel features of the present invention will become apparent to one of ordinary skill in the art upon consideration of the following examples, which are not intended to limit the scope of the invention in any way.

EXAMPLES

Example 1

Structure-Based Design of D-Amino Acid Peptide Inhibitors of Tau Fibrillation

Figure 4A:
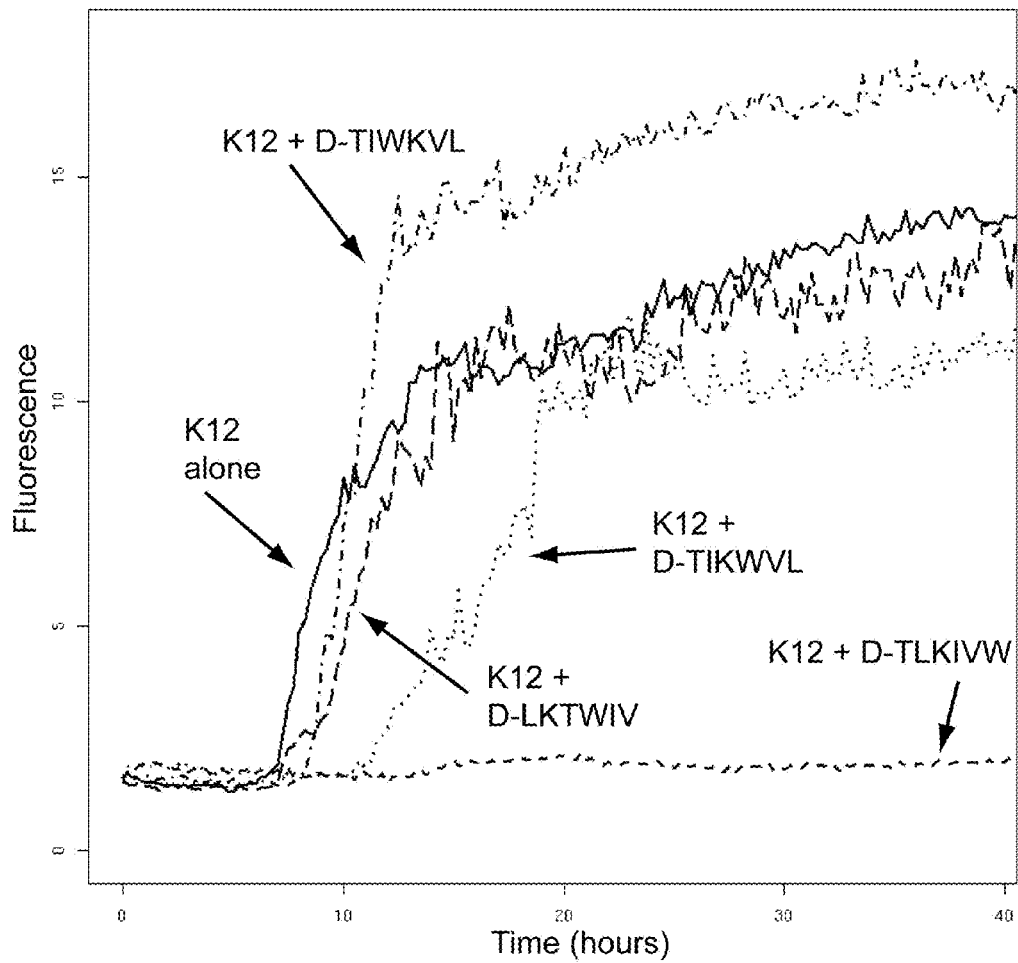
In FIG. 4(a), scrambling the order of the amino acids in D-TLKIVW demonstrates that the sequence order in D-TLKIVW is most effective in delaying the fibrillation of K12. Incubation with D-TLKIVW delays fibrillation relative to K12 alone. Incubation with the scrambled peptides D-TIKWVL, D-TIWKVL, and D-LKTWIV does not delay the onset of K12 fibrillation.
Figure 4B:
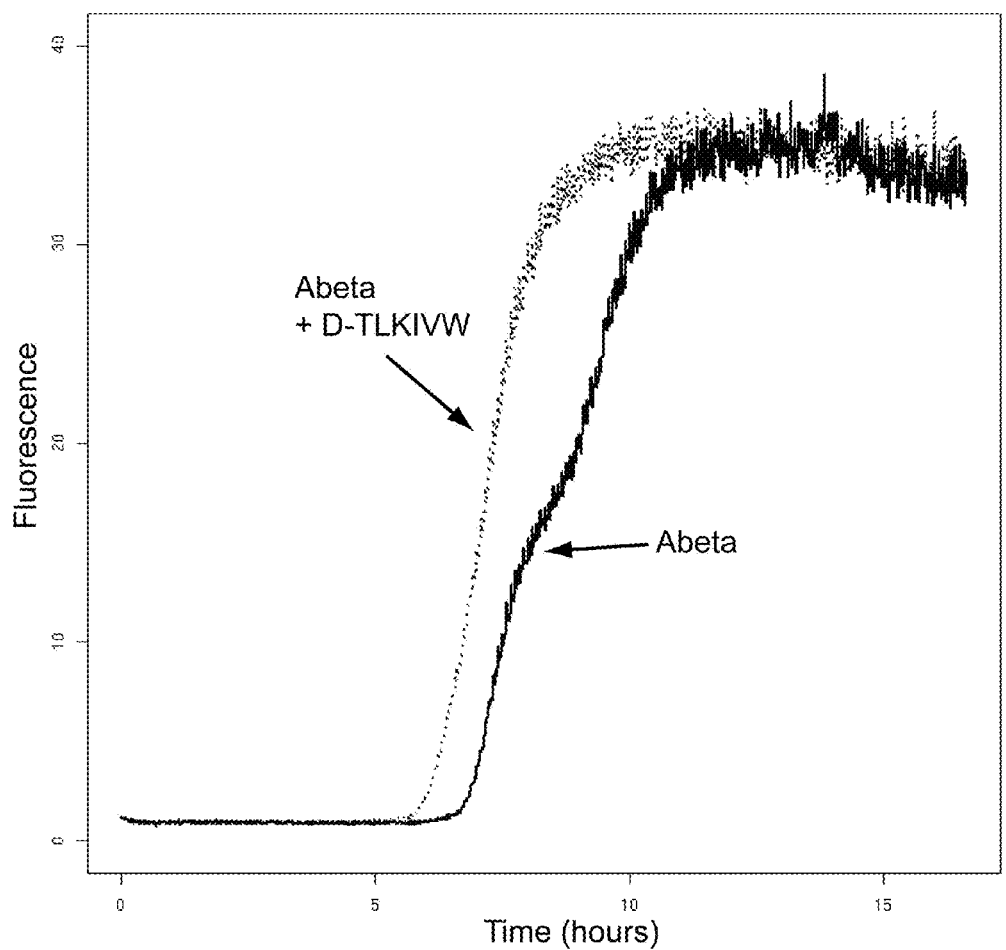
In FIG. 4(b), fibril formation of amyloid beta (abeta) protein is not delayed by addition of D-TLKIVW. Tau K12 fibrillation is monitored by ThS fluorescence and amyloid beta fibrillation is monitored by thioflavin T fluorescence.
Figure 4C:
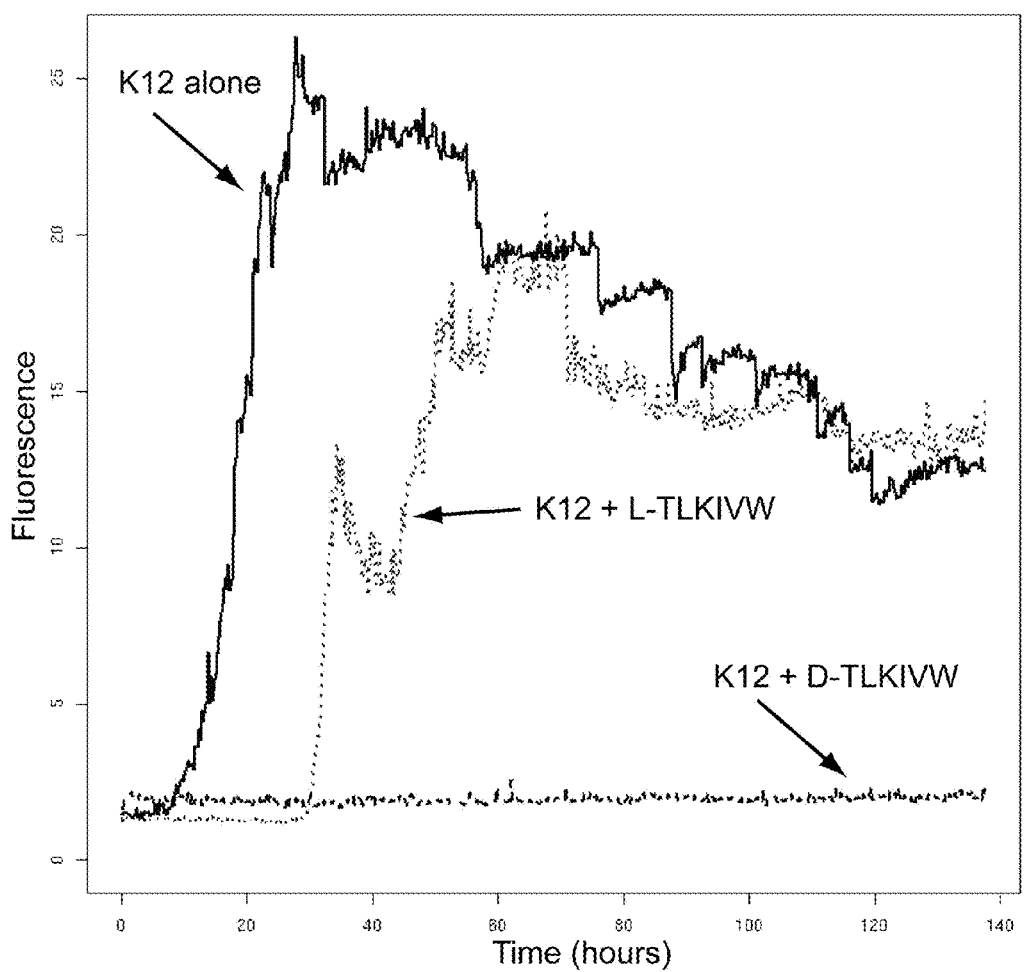
In FIG. 4(c), comparing inhibition by D-TLKIVW to its enantiomer shows that the presence of D-TLKIVW delays fibrillation much longer than L-TLKIVW (SEQ ID NO: 3) or K12 alone.
Figure 5:
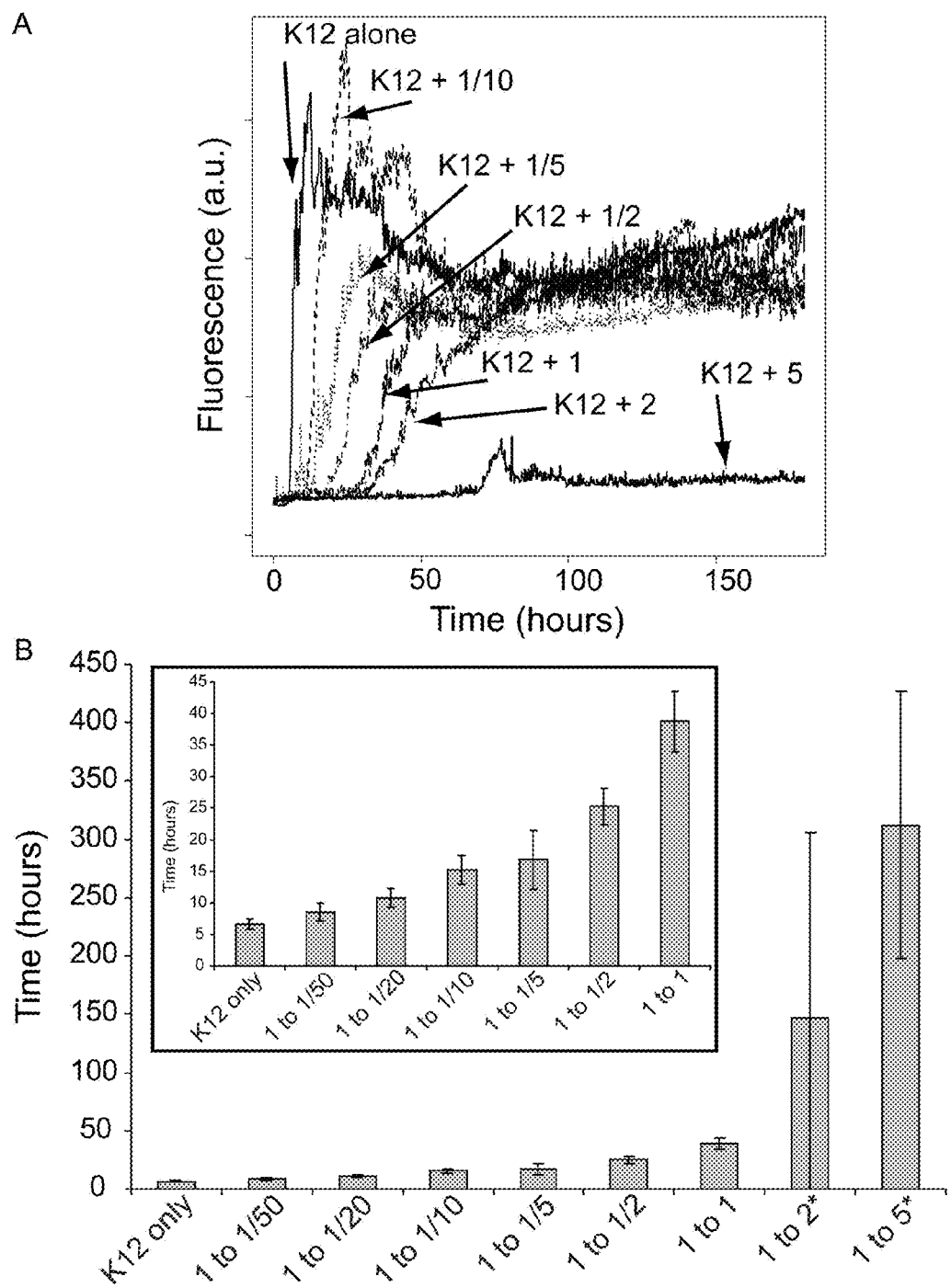
FIG. 5 demonstrates that D-TLKIVW delays the fibrillation of the tau construct K12 in a ratio dependent manner. Monitoring the fluorescence of ThS over time shows that the fibrillation of 50 µM K12 is delayed longer by higher concentrations of the D-peptide as shown in FIG. 5(a), which plots the mean fluorescence of 8 replicates over time (error bars not shown). D-TLKIVW shows an inhibitory effect even when present at only 2% the molar concentration as K12. The plots in FIG. 5(b) show the concentration dependence of the lag time for fibrillation to occur for each sample; the error bars represent the standard deviation of the lag time for the eight replicates at each ratio. Some of the samples where peptide was present at 2-fold and 5-fold excess did not show a ThS signal even after 300 hours, giving rise to the large error bars for these two ratios in this experiment. The inset in (b) expands the time axis to show the differences between the peptide ratios at lower concentrations of the D-peptide.
Figure 6:
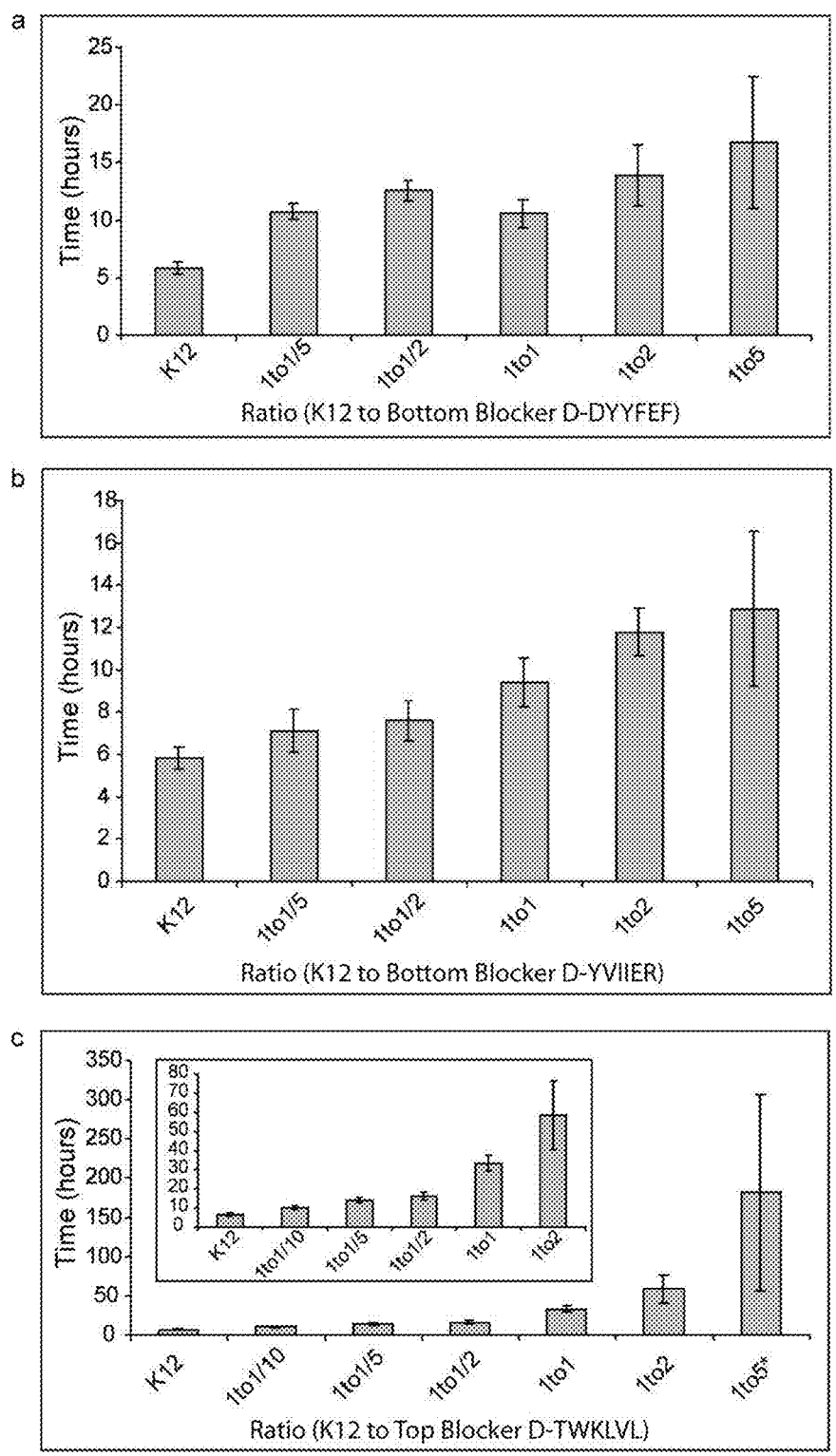
FIG. 6 demonstrates that three other D-amino acid inhibitory peptides delay the fibrillation of the tau construct K12 in a ratio dependent manner. Each plot shows the lag time in hours for tau fibrillation as monitored by ThS fluorescence.
Figure 7:
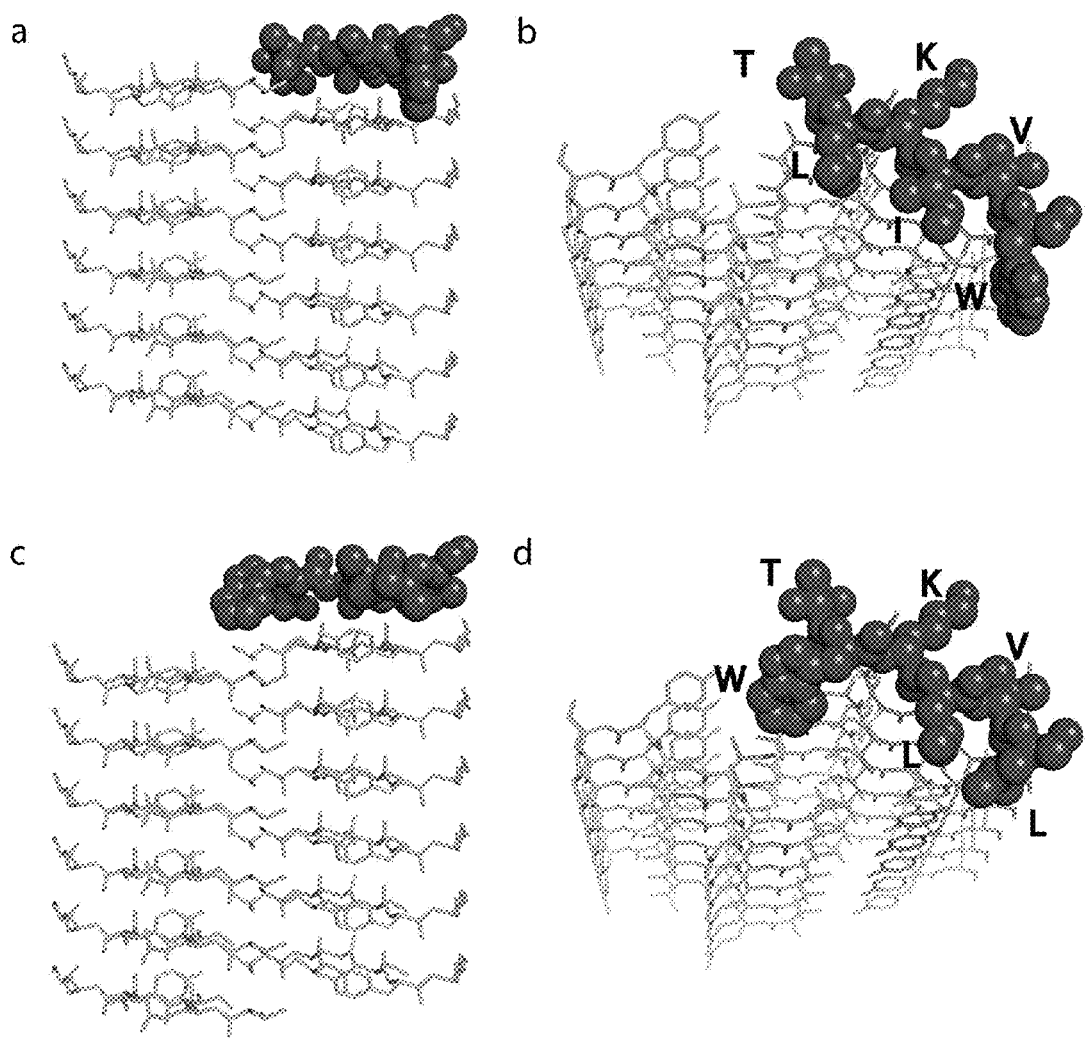
FIG. 7 depicts fibril blockers designed to interact with the top of VQIVYK (SEQ ID NO: 2).
Figure 8:
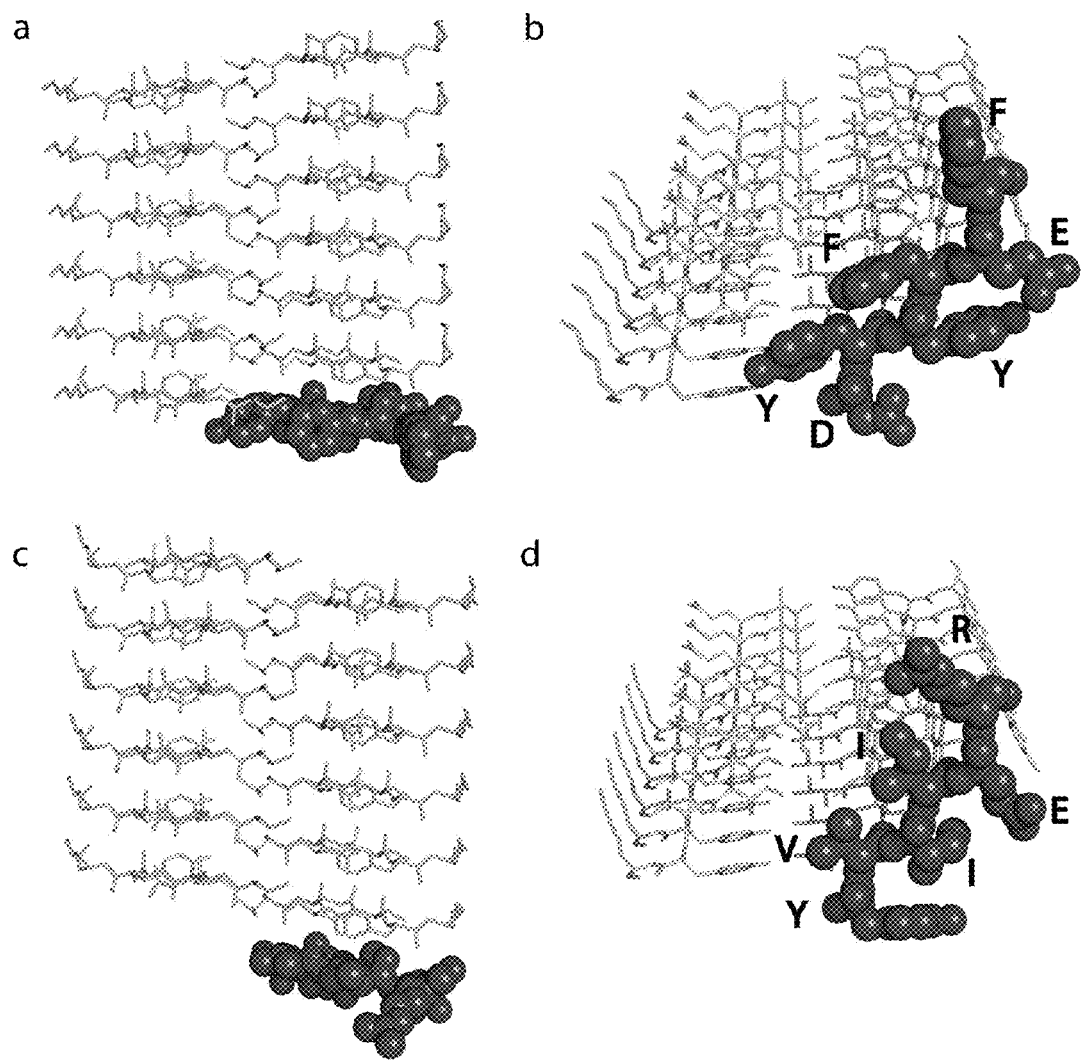
FIG. 8 depicts fibril blockers designed to interact with bottom of VQIVYK.
Figure 9:
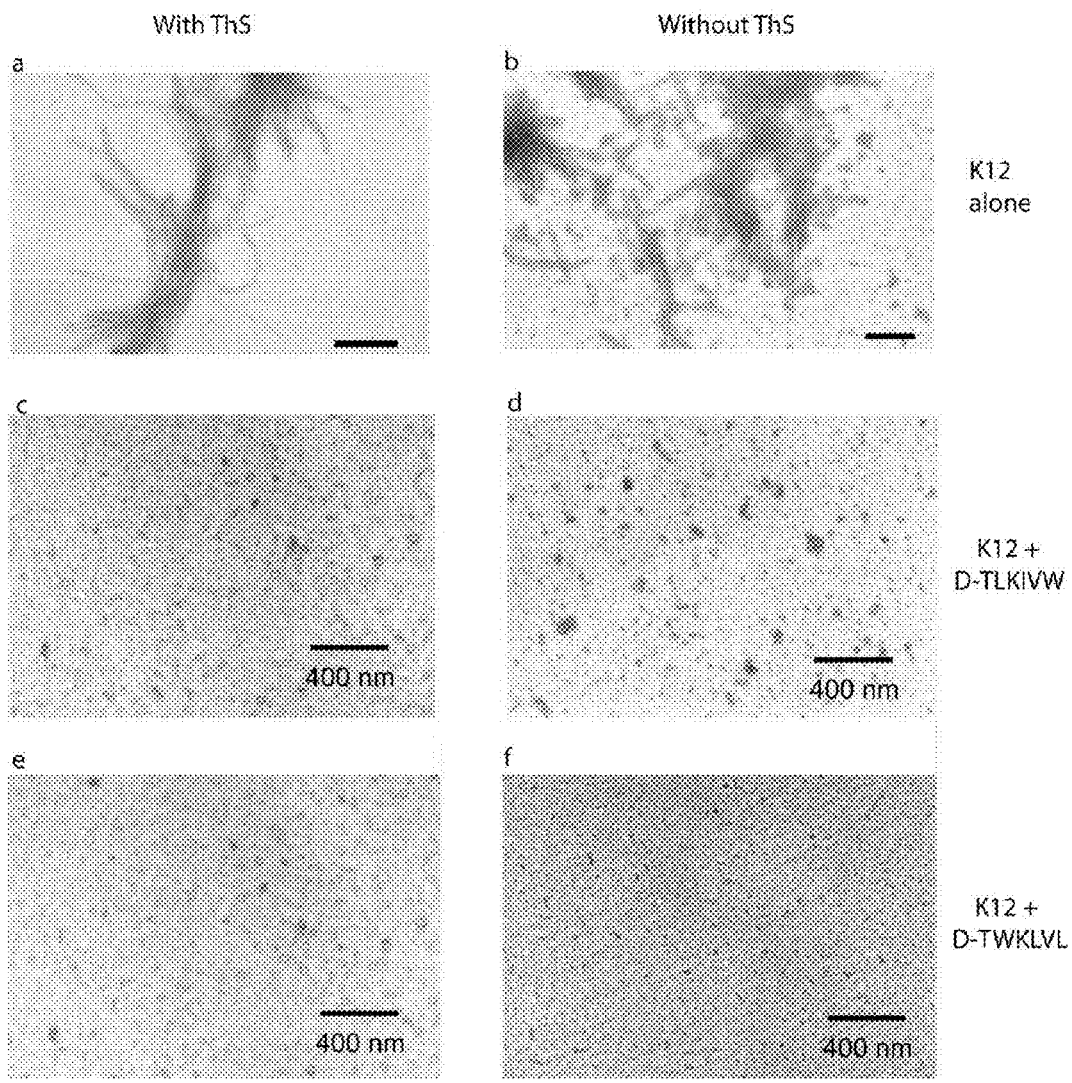
FIG. 9 presents a series of electron micrographs of K12 showing the effect of ThS on fibrillation. Characteristic micrographs from fibrillation experiments of K12 verify that fibrils do not form in the presence of peptides and ThS has little effect on fibrillation. On the left side in FIGS. 9(a), (c), and (e), the reaction proceeded with ThS present. On the right in FIGS. 9(b), (d), and (f), ThS was excluded from the reaction mixture.
Figure 10A:
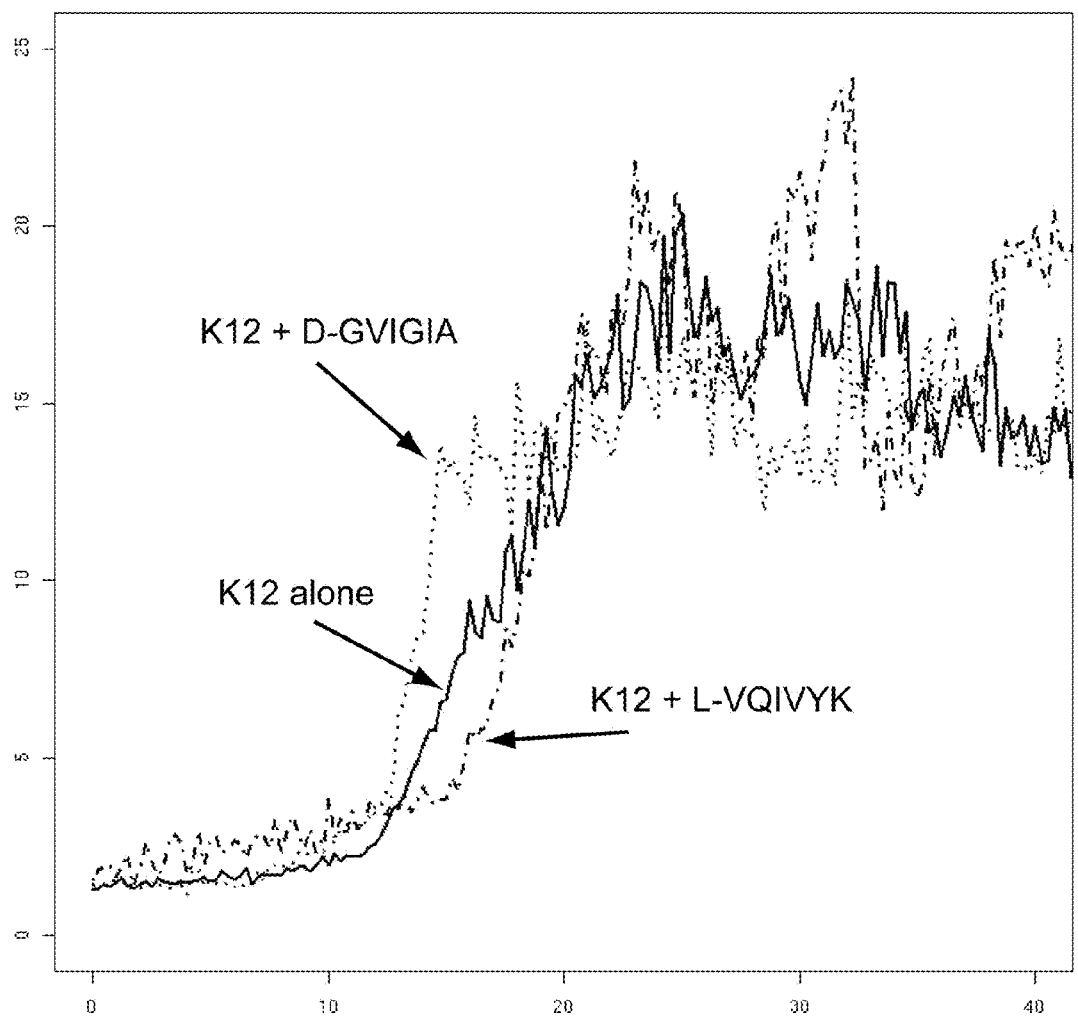
In FIG. 10(a), K12 was incubated with the peptide D-GVIGIA, without any effect on fibrillation. This control shows that not all D-amino acid peptides block fibril formation. The VQIVYK (SEQ ID NO: 2) peptide has no effect at equimolar concentrations or in excess (not shown) compared to K12 alone.
Figure 10B:
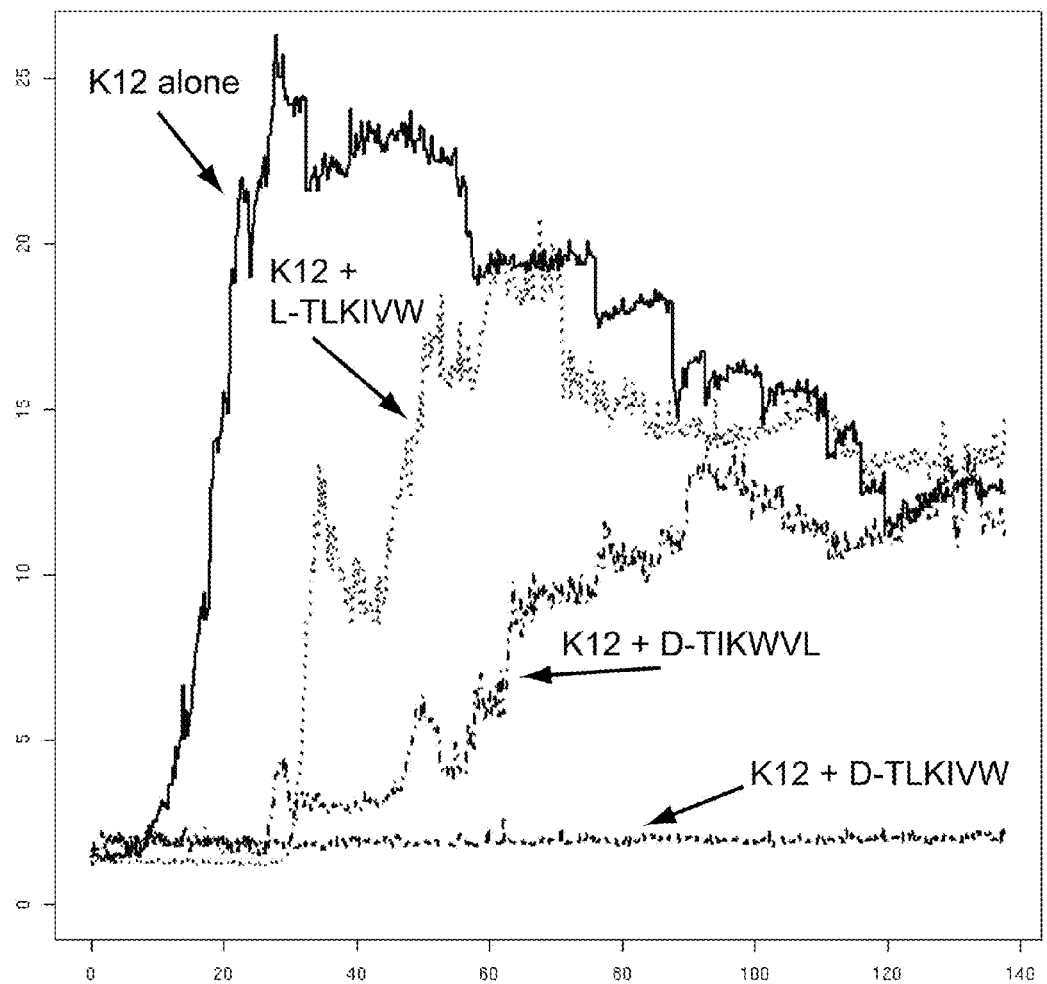
In FIG. 10(b), the plot shows that L-TLKIVW (SEQ ID NO: 3) and D-TIKWVL, a peptide with the order of side chains scrambled, are not nearly as effective as D-TLKIVW at inhibiting the fibrillation of K12.
Figure 11:
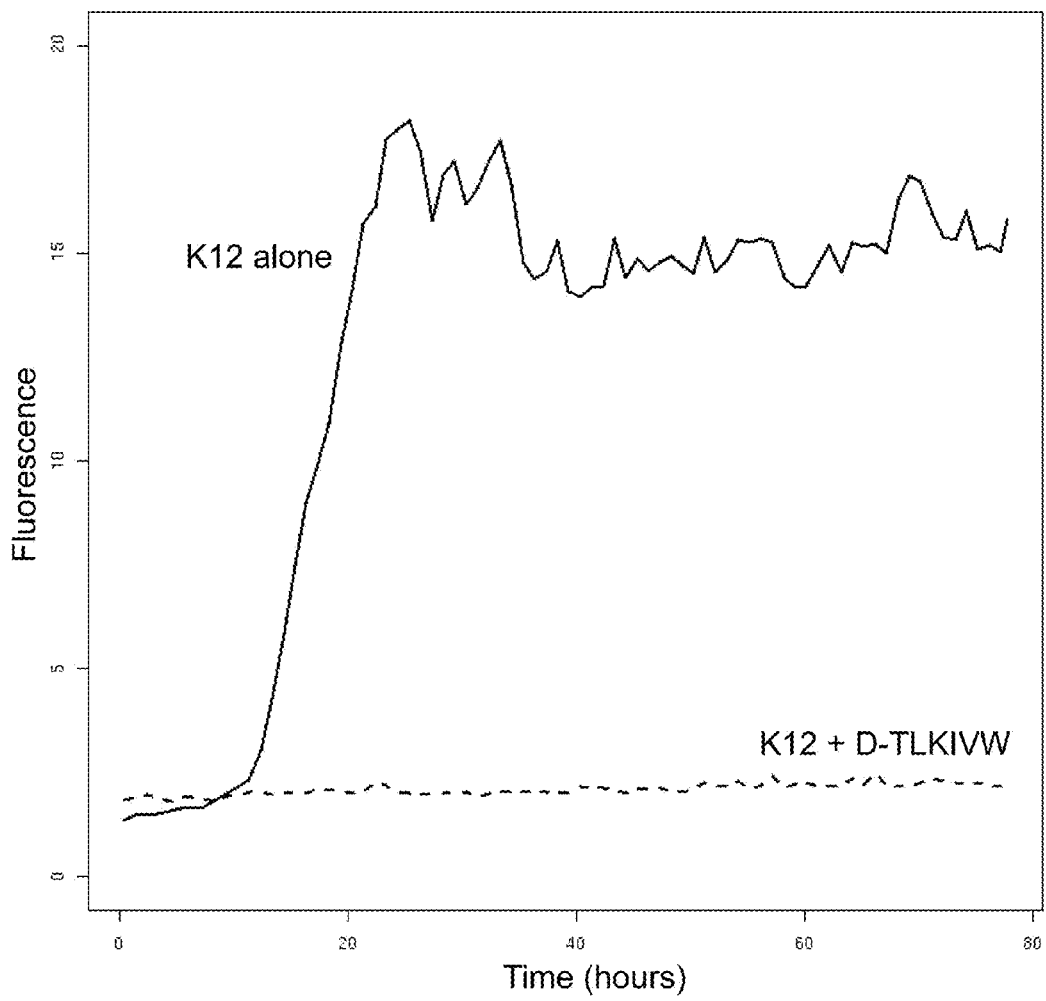
FIG. 11 depicts fluorescence monitoring of fibril formation with thioflavin S (ThS). Fibril formation is monitored by ThS fluorescence (in arbitrary units) over time (in hours). As fibrils form, a fluorescence signal is demonstrated. In equimolar concentrations, the D-amino acid peptide TLKIVW (SEQ ID NO: 4) prevents the formation of K12fibrils, as shown when compared to K12 alone.

To design D-amino acid peptides that disrupt fibril formation, a procedure was adopted that is analogous to mirror image phage display techniques. D-amino acid peptides were designed that can cap the end of the known structure of the VQIVYK (SEQ ID NO: 2) steric zipper (M. R. Sawaya et al., Nature 447, 453 (May 24, 2007)). These peptides can inhibit the fibril formation of the tau protein. The methods involve reversing the stereochemistry of the steric zipper structure (which is built from L-amino acids) to create a virtual D-amino acid structure of the steric zipper. Because of the polarity of the fibril axis found in the steric zipper structure, we designed peptide caps for both the top and bottom of the steric zipper. The RosettaDesign algorithm was used to build a set of L-rotamers and selected those that would favorably interact with the D-amino acid steric zipper (B. Kuhlman et al., Science 302, 1364 (Nov. 21, 2003)). The RosettaDesign algorithm optimizes properties important for protein stability. After the computational design of the L-amino acid inhibitor peptides against the D-amino acid steric zipper, the virtual stereochemistry is reversed to synthesize D-amino acid fibril blockers of the L-amino acid steric zipper. For example, the four peptides D-TLKIVW, D-TWKLVL, D-YVIIER and D-DYYFEK were suitable fibril blockers for each design template we used (FIGS. 7 and 8). As shown in FIGS. 7 and 8, the peptides pack favorably with the VQIVYK (SEQ ID NO: 2) segment structure. Residues chosen make specific hydrophobic contacts with the side chains in the steric zipper (FIGS. 7 and 8). For example, one effective strategy was to maintain all of the main chain hydrogen bonding and replace the hydrogen bonding and tyrosine stacking from the VQIVYK (SEQ ID NO: 2) structure with other van der waal interactions (FIG. 2). For designing top blockers, one peptide was designed to bind to both β-strands at the top of the paired β-sheet structure (FIG. 7*a*) and a second blocker was designed that primarily binds to only one of the β-strands at the top of the fibril-like structure (FIG. 7*b*). Similarly, two bottom blockers were designed (FIGS. 7*c,d* and 8*c,d*). The placement of the inhibitory peptides on the VQIVYK (SEQ ID NO: 2) structure in the model makes further addition of other VQIVYK (SEQ ID NO: 2) segments energetically unfavorable.

Example 2

Inhibition of K12 Fibrillation with D-Amino Acid Peptide Inhibitors

The following describes the experimental methods used to evaluate the inhibitory effects of the D-peptides described above.

Materials and Methods

All peptides were purchased from CS Bio Co. Peptides were dissolved at 0.5 mM in 250 mM phosphate buffer immediately before fibril inhibition assays. ThS was obtained from MP Biomedicals, Inc. Heparin (average MW of 18000) was obtained from Sigma.

K12 Expression and Purifications

The expression vector pNG2, a derivative of pET-3b (Studier et al., 1990), containing the K12 gene, was generously provided by E. Mandelkow (Biernat et al., 1992). We used the BL21 (DE3) *E. coli* for expression (Studier et al., 1990). K12 was purified based on previously described methods (Barghorn et al., 2005). In short, the cell pellet was resuspended in 20 mM MES pH 6.8, 1 mM EDTA, 0.2 mM $MgCl_2$, 5 mM DTT, 1 mM PMSF, and a protease inhibitor cocktail. The cells were sonicated for 3 minutes and following addition of NaCl to bring cell lysate to 0.5 M NaCl, the lysate was boiled for 20 minutes. The lysate was dialysed twice against 20 mM MES pH 6.8, 50 mM NaCl, 1 mM EDTA, 1 mM $MgCl_2$, 2 mM DTT, and 0.1 mM PMSF. We used cation exchange chromatography, eluting with 20 mM MES pH 6.8, 1 M NaCl, 1 mM EDTA, 1 mM $MgCl_2$, 2 mM DTT, and 0.1 mM PMSF, optionally followed by size exclusion with a Superdex™ 75 10/300 GL column (GE Healthcare) depending on preparation purity as assessed by SDS PAGE.

Fibril Formation Inhibition Assays

150 μL reactions containing 50 or 100 μM tau K12, as determined by the micro BCA Protein Assay Kit (Pierce), were incubated in 250 mM sodium phosphate buffer pH 7.4 with 1 mM DTT, 3 μM heparin, and 10 μM ThS (Friedhoff et al., 1998; Perez et al., 1996; Schweers et al., 1995). Peptides were dissolved in 250 mM sodium phosphate buffer pH 7.4 and added at various molar ratios to the reaction mixtures. The fluorescence signal was measured every 15 minutes with excitation and emission wavelengths of 440 and 510 nm, respectively, at 37° C. with continuous shaking at 900 rpm with a diameter of 1 mm in a Varioskan plate reader (Thermo Fisher Scientific, Inc.). Reactions were split into a minimum of 3 replicates in Nunc optically clear bottom, 96-well black plates, sealed with Corning pressure seal tape and monitored for various times. Each experiment was repeated a minimum of four times yielding the same results.

Electron Microscopy

5 μL of sample were applied to glow discharged 400 mesh carbon-coated formar films on copper grids (Ted Pella, Inc.) for three minutes. Grids were rinsed twice with distilled water and stained with 1% uranyl acetate for 90 seconds. Grids were examined in a Hitachi H-7000 transmission electron microscope at 75 kEv.

Results

Peptides inhibit tau fibrillation. Fibrillation of the tau K12 construct was monitored by following the increase in the fluorescence of Thioflavine S (ThS) and viewing samples by electron microscopy. Each D-amino acid cap inhibited fibril formation at a different concentration relative to K12. At higher cap concentrations, the lag time of K12 fibrillation increased exponentially for the best blockers (FIGS. 5 and 6). At equimolar ratios, all peptides except D-DYYFEK systematically delayed fibrillation (FIG. 3*a*). The blocker D-DYYFEK was replaced by D-DYYFEF because the Phe in the sixth position was also predicted to be an effective inhibitor. D-DYYFEF showed improved capping over D-DYYFEK. D-TLKIVW, designed to interact with the top of the VQIVYK (SEQ ID NO: 2) fibril, is the most effective peptide. The cap delays fibril formation even when present at only 5-10% of the molar concentration of K12(FIG. 5*a,b*). At higher ratios of D-TLKIVW, such as 2-fold or 5-fold excess peptide, some experiment replicates did not form fibrils after more than 2 weeks (FIG. 5*b*). D-TWKLVL, also designed to interact with the top of the VQIVYK (SEQ ID NO: 2) β-sheet structure, was another potent inhibitor, with a mild inhibitory effect at 10% the molar concentration of K12, but effective inhibition for about 1 week at 5-fold excess peptide (FIG. 6*c*). D-DYYFEF and D-YVIIER both delayed K12 fibrillation in a concentration dependent manner, similar to the other two peptide blockers, but with less of a delay on the lag time (FIG. 6*a,b*). FIG. 9 shows micrographs of tau K12 incubated with D-TLKIVW and DTWKLVL. When K12 incubated with either peptide, small circular and irregular particles were observed, but there were no fibrils (FIG. 9*c-f*). In contrast, K12 under the same conditions forms numerous fibrils in the absence of capping peptides. Using electron microscopy, it has been confirmed that ThS does not affect fibrillation or inhibition. K12 forms fibrils with similar morphology with and without ThS present (FIG. 9*a,b*) and the inhibition by the peptides also appears to be independent of the presence of ThS (FIG. 9*c-f*).

Sequence Specific Inhibition. Several control peptides showed that the designed caps are potent compared to non-designed sequences. We anticipated that the L-VQIVYK (SEQ ID NO: 1) peptide may affect fibril formation. However, L-VQIVYK (SEQ ID NO: 1) had no significant effect on fibrillation (FIG. 10*a*). Similarly, a D-amino acid control peptide, D-GVIGIA, a stereoisomer of an L-amino acid peptide known to aggregate on its own, showed no effect on fibrillation (FIG. 10*a*). The order of the residues was scrambled in one face of the inhibitor D-TLKIVW. The resulting peptide, D-TIKWVL, showed some inhibitory effect at an equimolar ratio with K12 with an average lag time of 54 hours compared to over 140 hours for D-TLKIVW (FIG. 10b). Similarly, the L-amino acid peptide, L-TLKIVW (SEQ ID NO: 3), was able to inhibit fibril formation, but not nearly as long as D-TLKIVW (FIG. 10b). The average lag time of eight replicates of L-TLKIVW (SEQ ID NO: 3) inhibition was about 40 hours (FIG. 10b). D-TLKIVW was also tested for specificity on other fibril forming systems. When incubated with the amyloid β protein, D-TLKIVW showed no effect on fibrillation, suggesting that the interaction is specific for the VQIVYK (SEQ ID NO: 2) interface (FIG. 4b).

These examples illustrate possible embodiments of the present invention. As one of skill in the art will appreciate, because of the versatility of the compositions, kits, and methods of using the compositions disclosed herein, the compositions, kits, and methods can be used in other similar ways to those described herein. Thus, while the invention has been particularly shown and described with reference to some embodiments thereof, it will be understood by those skilled in the art that they have been presented by way of example only, and not limitation, and various changes in form and details can be made therein without departing from the spirit and scope of the invention. Therefore, the breadth and scope of the present invention should not be limited by any of the above-described exemplary embodiments, but should be defined only in accordance with the following paragraphs and their equivalents. All cited references are incorporated by reference, in their entirety and for all purposes, as if each had been individually incorporated by reference.

References

Avila, J. (2000). Tau aggregation into fibrillar polymers: taupathies. FEBS Lett 476, 89-92.

Barghorn, S., Biernat, J., and Mandelkow, E. (2005). Purification of recombinant tau protein and preparation of Alzheimer-paired helical filaments in vitro. Methods Mol Biol 299, 35-51.

Berriman, J., Serpell, L. C., Oberg, K. A., Fink, A. L., Goedert, M., and Crowther, R. A. (2003). Tau filaments from human brain and from in vitro assembly of recombinant protein show cross-beta structure. Proc Natl Acad Sci U S A 100, 9034-9038.

Biernat, J., Mandelkow, E. M., Schroter, C., Lichtenberg-Kraag, B., Steiner, B., Berling, B., Meyer, H., Mercken, M., Vandermeeren, A., Goedert, M., and et al. (1992). The switch of tau protein to an Alzheimer-like state includes the phosphorylation of two serine-proline motifs upstream of the microtubule binding region. Embo J 11, 1593-1597.

Chalifour, R. J., McLaughlin, R. W., Lavoie, L., Morissette, C., Tremblay, N., Boule, M., Sarazin, P., Stea, D., Lacombe, D., Tremblay, P., and Gervais, F. (2003). Stereoselective interactions of peptide inhibitors with the beta-amyloid peptide. J Biol Chem 278, 34874-34881.

Cruz, M., Tusell, J. M., Grillo-Bosch, D., Albericio, F., Serratosa, J., Rabanal, F., and Giralt, E. (2004). Inhibition of beta-amyloid toxicity by short peptides containing N-methyl amino acids. J Pept Res 63, 324-328.

Dobson, C. M. (1999). Protein misfolding, evolution and disease. Trends Biochem Sci 24, 329-332.

Doig, A. J., Hughes, E., Burke, R. M., Su, T. J., Heenan, R. K., and Lu, J. (2002). Inhibition of toxicity and protofibril formation in the amyloid-beta peptide beta(25-35) using N-methylated derivatives. Biochem Soc Trans 30, 537-542.

Eanes, E. D., and Glenner, G. G. (1968). X-ray diffraction studies on amyloid filaments. J Histochem Cytochem 16, 673-677.

Esteras-Chopo, A., Pastor, M. T., Serrano, L., and Lopez de la Paz, M. (2008). New Strategy for the Generation of Specific d-Peptide Amyloid Inhibitors. J Mol Biol.

Ferrao-Gonzales, A. D., Robbs, B. K., Moreau, V. H., Ferreira, A., Juliano, L., Valente, A. P., Almeida, F. C., Silva, J. L., and Foguel, D. (2005). Controlling {beta}-amyloid oligomerization by the use of naphthalene sulfonates: trapping low molecular weight oligomeric species. J Biol Chem 280, 34747-34754.

Findeis, M. A., Musso, G. M., Arico-Muendel, C. C., Benjamin, H. W., Hundal, A. M., Lee, J. J., Chin, J., Kelley, M., Wakefield, J., Hayward, N. J., and Molineaux, S. M. (1999). Modified-peptide inhibitors of amyloid beta-peptide polymerization. Biochemistry 38, 6791-6800.

Friedhoff, P., Schneider, A., Mandelkow, E. M., and Mandelkow, E. (1998). Rapid assembly of Alzheimer-like paired helical filaments from microtubule-associated protein tau monitored by fluorescence in solution. Biochemistry 37, 10223-10230.

Goedert, M., Spillantini, M. G., and Davies, S. W. (1998). Filamentous nerve cell inclusions in neurodegenerative diseases. Curr Opin Neurobiol 8, 619-632.

Gordon, D. J., Sciarretta, K. L., and Meredith, S. C. (2001). Inhibition of beta-amyloid(40) fibrillogenesis and disassembly of beta-amyloid(40) fibrils by short beta-amyloid congeners containing N-methyl amino acids at alternate residues. Biochemistry 40, 8237-8245.

Goux, W. J., Kopplin, L., Nguyen, A. D., Leak, K., Rutkofsky, M., Shanmuganandam, V. D., Sharma, D., Inouye, H., and Kirschner, D. A. (2004). The formation of straight and twisted filaments from short tau peptides. J Biol Chem 279, 26868-26875.

Harkany, T., Mulder, J., Sasvari, M., Abraham, I., Konya, C., Zarandi, M., Penke, B., Luiten, P. G., and Nyakas, C. (1999). N-Methyl-D-aspartate receptor antagonist MK-801 and radical scavengers protect cholinergic nucleus basalis neurons against beta-amyloid neurotoxicity. Neurobiol Dis 6, 109-121.

Hughes, E., Burke, R. M., and Doig, A. J. (2000). Inhibition of toxicity in the beta-amyloid peptide fragment beta -(25-35) using N-methylated derivatives: a general strategy to prevent amyloid formation. J Biol Chem 275, 25109-25115.

Kapurniotu, A., Schmauder, A., and Tenidis, K. (2002). Structure-based design and study of non-amyloidogenic, double N-methylated IAPP amyloid core sequences as inhibitors of IAPP amyloid formation and cytotoxicity. J Mol Biol 315, 339-350.

Klabunde, T., Petrassi, H. M., Oza, V. B., Raman, P., Kelly, J. W., and Sacchettini, J. C. (2000). Rational design of potent human transthyretin amyloid disease inhibitors. Nat Struct Biol 7, 312-321

Kokkoni, N., Stott, K., Amijee, H., Mason, J. M., and Doig, A. J. (2006). N-Methylated Peptide Inhibitors of Amyloid Aggregation and Toxicity. Optimization of the Inhibitor Structure. Biochemistry 45, 9906-9918.

Kondo, J., Honda, T., Mori, H., Hamada, Y., Miura, R., Ogawara, M., and Ihara, Y. (1988). The carboxyl third of tau is tightly bound to paired helical filaments. Neuron 1, 827-834.

Kortemme, T., Joachimiak, L. A., Bullock, A. N., Schuler, A. D., Stoddard, B. L., and Baker, D. (2004). Computational redesign of protein-protein interaction specificity. Nat Struct Mol Biol 11, 371-379.

Kuhlman, B., Dantas, G., Ireton, G. C., Varani, G., Stoddard, B. L., and Baker, D. (2003). Design of a novel globular protein fold with atomic-level accuracy. Science 302, 1364-1368.

LeVine, H., 3rd (1993). Thioflavine T interaction with synthetic Alzheimer's disease beta-amyloid peptides: detection of amyloid aggregation in solution. Protein Sci 2, 404-410.

Nelson, R., Sawaya, M. R., Balbirnie, M., Madsen, A. O., Riekel, C., Grothe, R., and Eisenberg, D. (2005). Structure of the cross-beta spine of amyloid-like fibrils. Nature 435, 773-778.

Ono, K., Hasegawa, K., Naiki, H., and Yamada, M. (2004). Curcumin has potent anti- amyloidogenic effects for Alzheimer's beta-amyloid fibrils in vitro. J Neurosci Res 75, 742-750.

Ono, K., Hasegawa, K., Naiki, H., and Yamada, M. (2004). Anti-amyloidogenic activity of tannic acid and its activity to destabilize Alzheimer's beta-amyloid fibrils in vitro. Biochim Biophys Acta 1690, 193-202.

Ono, K., Hasegawa, K., Yamada, M., and Naiki, H. (2002). Nicotine breaks down preformed Alzheimer's beta-amyloid fibrils in vitro. Biol Psychiatry 52, 880-886.

Ono, K., Yoshiike, Y., Takashima, A., Hasegawa, K., Naiki, H., and Yamada, M. (2004). Vitamin A exhibits potent antiamyloidogenic and fibril-destabilizing effects in vitro. Exp Neurol 189, 380-392.

Perez, M., Valpuesta, J. M., Medina, M., Montejo de Garcini, E., and Avila, J. (1996). Polymerization of tau into filaments in the presence of heparin: the minimal sequence required for tau-tau interaction. J Neurochem 67, 1183-1190.

Petrassi, H. M., Johnson, S. M., Purkey, H. E., Chiang, K. P., Walkup, T., Jiang, X., Powers, E. T., and Kelly, J. W. (2005). Potent and selective structure-based dibenzofuran inhibitors of transthyretin amyloidogenesis: kinetic stabilization of the native state. J Am Chem Soc 127, 6662-6671.

Petrassi, H. M., Klabunde, T., Sacchettini, J., and Kelly, J. W. (2000). Structure-Based Design of N-Phenyl Phenoxazine Transthyretin Amyloid Fibril Inhibitors. J Am Chem Soc 122, 2178-2192.

Rzepecki, P., Nagel-Steger, L., Feuerstein, S., Linne, U., Molt, O., Zadmard, R., Aschermann, K., Wehner, M., Schrader, T., and Riesner, D. (2004). Prevention of Alzheimer's disease-associated Abeta aggregation by rationally designed nonpeptidic beta-sheet ligands. J Biol Chem 279, 47497-47505.

Sato, T., Kienlen-Campard, P., Ahmed, M., Liu, W., Li, H., Elliott, J. I., Aimoto, S., Constantinescu, S. N., Octave, J. N., and Smith, S. O. (2006). Inhibitors of amyloid toxicity based on beta-sheet packing of Abeta40 and Abeta42. Biochemistry 45, 5503-5516.

Sawaya, M. R., Sambashivan, S., Nelson, R., Ivanova, M. I., Sievers, S. A., Apostol, M. I., Thompson, M. J., Balbirnie, M., Wiltzius, J. J., McFarlane, H. T., et al. (2007). Atomic structures of amyloid cross-beta spines reveal varied steric zippers. Nature 447, 453-457.

Schumacher, T. N., Mayr, L. M., Minor, D. L., Jr., Milhollen, M. A., Burgess, M. W., and Kim, P.S. (1996). Identification of D-peptide ligands through mirror-image phage display. Science 271, 1854-1857.

Schweers, O., Mandelkow, E. M., Biernat, J., and Mandelkow, E. (1995). Oxidation of cysteine-322 in the repeat domain of microtubule-associated protein tau controls the in vitro assembly of paired helical filaments. Proc Natl Acad Sci U S A 92, 8463-8467.

Selkoe, D.J. (2001). Alzheimer's disease: genes, proteins, and therapy. Physiol Rev 81, 741-766.

Sipe, J. D., and Cohen, A. S. (2000). Review: history of the amyloid fibril. J Struct Biol 130, 88-98.

Soto, C., Kindy, M. S., Baumann, M., and Frangione, B. (1996). Inhibition of Alzheimer's amyloidosis by peptides that prevent beta-sheet conformation. Biochem Biophys Res Commun 226, 672-680.

Soto, C., Sigurdsson, E. M., Morelli, L., Kumar, R. A., Castano, E. M., and Frangione, B. (1998). Beta-sheet breaker peptides inhibit fibrillogenesis in a rat brain model of amyloidosis: implications for Alzheimer's therapy. Nat Med 4, 822-826.

Studier, F. W., Rosenberg, A. H., Dunn, J. J., and Dubendorff, J. W. (1990). Use of T7 RNA polymerase to direct expression of cloned genes. Methods Enzymol 185, 60-89.

Tatarek-Nossol, M., Yan, L. M., Schmauder, A., Tenidis, K., Westermark, G., and Kapurniotu, A. (2005). Inhibition of MAPP amyloid-fibril formation and apoptotic cell death by a designed MAPP amyloid- core-containing hexapeptide. Chem Biol 12, 797-809.

Tjernberg, L.O., Lilliehook, C., Callaway, D. J., Naslund, J., Hahne, S., Thyberg, J., Terenius, L., and Nordstedt, C. (1997). Controlling amyloid beta-peptide fibril formation with protease-stable ligands. J Biol Chem 272, 12601-12605.

Tjernberg, L.O., Naslund, J., Lindqvist, F., Johansson, J., Karlstrom, A. R., Thyberg, J., Terenius, L., and Nordstedt, C. (1996). Arrest of beta-amyloid fibril formation by a pentapeptide ligand. J Biol Chem 271, 8545-8548.

von Bergen, M., Friedhoff, P., Biernat, J., Heberle, J., Mandelkow, E. M., and Mandelkow, E. (2000). Assembly of tau protein into Alzheimer paired helical filaments depends on a local sequence motif ((306)VQIVYK(311)) (SEQ ID NO :2) forming beta structure. Proc Natl Acad Sci U S A 97, 5129-5134.

Westermark, P., Benson, M.D., Buxbaum, J.N., Cohen, A.S., Frangione, B., Ikeda, S., Masters, C. L., Merlini, G., Saraiva, M. J., and Sipe, J. D. (2007). A primer of amyloid nomenclature. Amyloid 14, 179-183.

Wiesehan, K., Buder, K., Linke, R. P., Patt, S., Stoldt, M., Unger, E., Schmitt, B., Bucci, E., and Willbold, D. (2003). Selection of D-amino-acid peptides that bind to Alzheimer's disease amyloid peptide abeta1-42 by mirror image phage display. Chembiochem 4, 748-753.

Wiesehan, K., Stohr, J., Nagel-Steger, L., van Groen, T., Riesner, D., and Willbold, D. (2008). Inhibition of cytotoxicity and amyloid fibril formation by a D-amino acid peptide that specifically binds to Alzheimer's disease amyloid peptide. Protein Eng Des Sel.

Wille, H., Drewes, G., Biernat, J., Mandelkow, E. M., and Mandelkow, E. (1992). Alzheimer-like paired helical filaments and antiparallel dimers formed from microtubuleassociated protein tau in vitro. J Cell Biol 118, 573-584.

Wischik, C.M., Novak, M., Thogersen, H.C., Edwards, P.C., Runswick, M.J., Jakes, R., Walker, J.E., Milstein, C., Roth, M., and Klug, A. (1988). Isolation of a fragment of tau derived from the core of the paired helical filament of Alzheimer disease. Proc Natl Acad Sci U S A 85, 4506-4510.

The invention claimed is:

1. A computer-implemented method for identifying and making an inhibitory peptidic compound that inhibits aggregation of an amyloid-forming target polypeptide, comprising the steps of:
identifying a template peptide sequence comprising a zipper-forming sequence or a mirror of the zipper-forming sequence from the target polypeptide, wherein the zipper-forming sequence aggregates into a steric zipper;
designing on a computer at least one complementary peptide sequence that forms favorable steric and energetic intermolecular interactions with the template peptide sequence, wherein the interactions occur at one or both of the upper or lower ends of the steric zipper; and
identifying a candidate inhibitory peptidic compound selected from the group consisting of the complementary sequence, a mirror of the complementary sequence, a peptide mimetic of the complementary sequence and a peptide mimetic of the mirror of the complementary sequence.

2. The method of claim 1, further comprising synthesizing the candidate inhibitory peptidic compound.

3. The method of claim 2, further comprising screening the candidate inhibitory peptidic compound for inhibiting aggregation of the target polypeptide.

4. The method of claim 1, wherein the candidate inhibitory peptidic compound comprises six amino acid residues.

5. The method of claim 1, wherein the target polypeptide is tau.

6. The method of claim 5, wherein the steric zipper sequence is L-VQIVYK (SEQ ID NO: 1).

7. The method of claim 6, wherein the candidate inhibitory peptidic compound is a peptide selected from the group consisting of D-TLKIVW (SEQ ID NO: 9), D-TWKLVL (SEQ ID NO: 10), D-YVIIER (SEQ ID NO: 11) and D-DYYFEF (SEQ ID NO: 12).

8. The method of claim 1, wherein the steric zipper has an upper and a lower end, and the candidate inhibitory peptidic compound binds to the upper end of the steric zipper.

9. The method of claim 1, wherein the steric zipper has an upper and a lower end, and the candidate inhibitory peptidic compound binds to the lower end of the steric zipper.

10. The method of claim 1, wherein the polypeptide is selected from the group consisting of α-synuclein, islet amyloid polypeptide, transthyretin, beta-2-microglobulin, prion protein (PrP), lysozyme, huntingtin protein and antibody light chain.

11. The method of claim 1, wherein the polypeptide is semen-derived enhancer of viral infection (SEVI).

12. The method of claim 1, wherein the peptidic compound comprises one or more D-amino acid residues.

13. The method of claim 1, wherein the inhibitory peptidic compound inhibits aggregation of an amyloid-forming target polypeptide in a disease or condition selected from the group consisting of Alzheimer's disease; Parkinson's disease (a-synuclein amyloidosis); amyotrophic lateral sclerosis; type II diabetes (islet amyloid polypeptide (IAPP) amyloidosis); lysozyme amyloidosis; familial and senile amyloidosis; the prion diseases variant Creutzfeldt-Jakob disease (vCJD) and Gerstmann-Sträussler-Scheinker syndrome (GSS); cardiac amyloidosis; human immunodeficiency virus (HIV) sexual transmission associated with the semen-derived enhancer of viral infection (SEVI) form of prostate activating protein of semen; and antibody light chain amyloidosis affecting kidney function.

14. The method of claim 1, wherein the at least one complementary peptide sequence comprises a binding moiety that binds to the zipper sequence and an inhibitory moiety that reduces aggregation of the target polypeptide.

* * * * *